United States Patent [19]

Kopin

[11] Patent Number: 5,541,071
[45] Date of Patent: Jul. 30, 1996

[54] ASSAY FOR IDENTIFYING ANTAGONISTS OF GASTRIN AND CCK-B RECEPTORS

[75] Inventor: Alan S. Kopin, Wellesley, Mass.

[73] Assignee: New England Medical Center Hospitals, Inc., Boston, Mass.

[21] Appl. No.: 978,892

[22] Filed: Nov. 12, 1992

Related U.S. Application Data

[63] Continuation-in-part of Ser. No. 941,373, Sep. 3, 1992, abandoned, which is a continuation-in-part of Ser. No. 832,841, Feb. 7, 1992, abandoned.

[51] Int. Cl.$^6$ .................. C12Q 1/02; C07K 14/705; C12N 5/00
[52] U.S. Cl. .................. 435/7.21; 435/69.1; 435/240.1; 435/254.11; 536/23.1; 530/350
[58] Field of Search ................ 435/69.1, 7.1, 435/7.21, 240.1, 252.3, 254.11, 6; 530/350; 43/240.2; 536/23.1

[56] References Cited

U.S. PATENT DOCUMENTS

| | | |
|---|---|---|
| 4,675,285 | 6/1987 Clark | 435/6 |
| 4,735,941 | 4/1988 Freidinger et al. | 514/220 |

FOREIGN PATENT DOCUMENTS

WOA9201055  1/1992  WIPO.
WOA9220814  11/1992  WIPO.

OTHER PUBLICATIONS

Hughes et al., PNAS, vol. 87, p. 6728, 1990.
Escobedo et al., 1988, Journal of Biological Chemistry, 263, 1482–1487.
Yu et al., 1990, Am. J. Physiol., 258, G86–G95.
Rudenko et al., "Characterization of brain gastrin cholecystokinin–binding proteins," Biosis Abstract No. 91058376 of article in Ukrainskii Biokhimicheskii Zhurnal (USSR), 62:26–30, 1990.
Park et al., "A new selective gastrin receptor antagonist: characterization via studies with isolated canine gastric parietal and d–cells," Abstract, Digestion 46:85–86, 1990.
Matozaki et al., "Characterization of cholecystokinin receptors in gastric chief cells . . . chief cells," Biosis Abstract No. 89499881 of article in Japanese Journal of Gastroenterology (Japan) 86:1424–1428, 1989.

Kopin et al., "Expression cloning and characterization of the canine parietal cell gastrin receptor," PNAS, USA, 89:3605–3609, 1992.
Pisegna et al., "Molecular cloning of the human brain and gastric cholecystokinin receptor: structure, functional . . . localization," Biochemical and Biophysical Research Communications 189:296–303, 1992.
Wank et al., "Purification, molecular cloning, and functional expression of the cholecystokinin receptor from rat pancreas," PNAS USA 89:3125–3129, 1992.
Stephen A. Wank et al., "Brain and gastrointestinal cholecystokinin receptor family: Structure and functional expression," Natl. Acad. Sci. USA, vol. 89, pp. 8691–8695, Sep. 1992.
Ira Gantz et al., "Molecular cloning of a gene encoding the histamine H2 receptor," Proc. Natl. Acad. Sci. USA vol. 88, pp. 429–433, Jan. 1991.
Dialog search, p. 1, Ira Gantz, "Molecular Cloning and Expression of the Gastric Receptor," Dialog file No. 265/266, Federal Research in Progress, I.D. No. 0001;78226;506, Jan. 1, 1991.
O'Hara et al., Society for Neuroscience Abstracts, vol. 16, Part 1, 1990.
Le T. Duong et al., "Purification and Characterization of the Rat Pancreatic Cholecystokinin Receptor," The Journal of Biological Chemistry, vol. 264, No. 30, pp. 17990–17996 Oct. 25, 1989.
J. Szecowka et al., "Purification of the pancreatic cholecystokinin receptor," Regulatory Peptides, vol. 24, pp. 215–224, Mar. 1989.
Yakabi et al., "Isolation and Purification of a 72KD Gastrin Receptor from Canine Gastric Parietal Cell Membranes," Gastroenterology, vol. 94, No. 5, p. A505, May 1988.

*Primary Examiner*—Stephen G. Walsh
*Assistant Examiner*—Sally P. Teng
*Attorney, Agent, or Firm*—Fish & Richardson P.C.

[57] ABSTRACT

The invention features purified nucleic acids encoding the mammalian gastrin/CCK-B receptor family. The invention also features a) the gastrin and CCK-B receptor polypeptides, b) a method of identifying antagonists to the gastrin or CCK-B receptors, and c) a parietal cell cDNA expression library.

5 Claims, 15 Drawing Sheets

```
  1 MELLKLNRSAQGSGAGPGASLCRAGGALLNSSGAGNLSCEPPRLRGAGTRELELAIRVTL  60
 61 YAVIFLMSVGGNVLIIVVLGLSRRLRTVTNAFLLSLAVSKLLLAVACMPFTLLPNLMGTF 120
121 IFGTVVCKAVSYLMGVSVSVSTLSLVAIALERYSAICRPLQARVWQTRSHAARVIIATWM 180
181 LSGLLMVPYPVYTAVQPAGGARALQCVHRWPSARVROTWSVLLLLLLFFVPGVVMAVAYG 240
241 LISRELYLGLRFDEDSDSESRVRSQGGLRGGAGPGPAPPNGSCRPEGGLAGEDGDGCYVQ 300
301 LPRSRQTLELSALTAPTPGPGGGPRPYQAKLLAKKRVVRMLLVIVVLFFLCWLPLYSANT 360
361 WRAFDSSGAHRALSGAPISFIHLLSYASACVNPLVYCFMHRRFRQACLETCARCCPRPPR 420
421 ARPRPLPDEDPPTPSIASLSRLSYTTISTLGPG 453
```

FIG. 1

```
         1                                                                49
GR-1     M E L L K L N R S A Q Q S G A Q P G A S L C R A Q Q A L L N S S G A G N L S C E P P R L R · G A G T
FC5      · · · · · · · · · · · · · · · · · · · · · · · M N S T L F S R V E · · N Y S V H Y N V S E N S D F L A F E N D D
hB2AR    · · · · · · · · · · · · · · · · · · · · · · · M G Q P G N G S A F L · · · · · L A P N R S H A P D H D V T 50                                                               96
GR-1     R E L E L A I R Y T L · · Y A V I F E M S V G G N Y L I I V V L G L S R R K L R T V T N A F L L S L
FC5      C H L P L A V I F T L A L A V G A V · I L G V S Q N L A L I I · L K Q K E N R N V T H I L I V N E
hB2AR    Q Q R D E V W V V G M G I V M S L I V L A I V F G N V L V I T A I A K F E R L Q T V T N Y F I T S L
                             —————————————————————————————
                                    I 97                                                              146
GR-1     A V S D L L A V A C M P F T L L P N E M Q T F I F Q T V V C K A V S Y L M G V S Y S D T L S L V
FC5      S F B D L L V A V M C L P F T F V Y T L M D H W V F G E T M C K L N P F V Q C V S I T V S I F S L V
hB2AR    A C A D L V M G L A V V P F G A A H I L M K M W T F G N F W C E F W T S I D V L C V T A S I E T L C
               ———————————————————————————
                       II                                        III 147                                                             193
GR-1     A I A L E R T S A I C R P L Q A R V W Q T R S H A A R V I A T W M L · · · S G L L M V P Y P V Y T
FC5      L A V E R H Q L I I N P · R G W · R P N N R H A Y I G I T V I N V L A V A S L P F V I T Q I L T
hB2AR    V I A V D R Y F A I T S P F K Y Q S L L T K N K A R V I I L M V W I V S G L T S F L P I Q M H W Y R
                                                   ———————————————————————
                                                            IV                         V 194                                                             238
GR-1     A · · · V Q P A G G A R A L Q C V H R W P B A R V W Q T W S V L L L L F F V P G V V M A V A
FC5      D E P F Q N W S L A W F K D K Y V C G E D K F P S D S H R L S Y T T L L L V Q Y F G P L C F I C
hB2AR    A T H Q E A I N C Y A N E T C C D F F · · · · T N Q A Y A I A S S I V S F Y V P L V I M V F V
                                                       ———————————————————————
```

FIG. 2A

```
                                                                    288
GR-1   ...VGL.SRELYLGLRFDEDSDSESRVRSGGLRGGAGPQPAPPNGSCRPEGG...
FC5    ...VFKI.....................................................
hB2AR  ...VSRVFQEAKRQLQKIDKSEGRFHVQNLSQVEQDGRTQHG..................

338
GR-1   LAGEDGDGCYVQLPRSRQTLELSALTAPTPGPGGGPRPYQAKLWAKKRVV
FC5    ..........VIRLKHRNNMMD...KIRDSKYRSSETKRIN
hB2AR  ..................LRRS....LKEHKAL

VI                                                          386
GR-1   RMLCVIVVLEFLCWLPLYSANTWRAFDSSGAHRALSGAPISFD..HLSY
FC5    VMLLSIVVAFAVCWLPLTFNT.VFQWNHQI.ATCNHNLLFLCHLTAM
hB2AR  KTLGIIMGTFTLCWLPFFIVNIVHVIQDNLIRKEV...YLLLNWIGY

VII                                                         426
GR-1   .....RFRACETCARCCP.RPPRARPRPC
FC5    ASACVNPFLVVCFMHR......N..RQRDLQFFNFCDFFHSRDQRTTRL
hB2AR  ISTCVNPIFYGFLNK...
       VNSGFNPLIYCRSPDFRIAFQELLCLRRSSLKAYGNGYSSNGNTQEQSGY

453
GR-1   .........PRTPSIASLSELSYTIATKGPQ...
FC5    PDED......................................
hB2AR  HVEQEKENKLLCEDLPGTEDFVGHQGTVPSDNIDSQGRNCSTNDSL...
```

FIG. 2B

- □ CCK-8
- ○ GASTRIN
- ■ des CCK-8
- ▨ L364,718
- △ L365,260

● TRANSFECTED
○ UNTRANSFECTED

5' TO 3'OF GR-1: CANINE GASTRIN RECEPTOR    ALAM S. KOPIN

FK-GR1-11-25-91    LENGTH: 1440    NOVEMBER 25, 1991    11:28    TYPE: N

CHECK: 3367

```
   1 GCCGGGGCCA TGGAGCTGCT AAAGCTGAAC CGGAGCGCGC AGGGGTCCGG AGCCGGGCCG   60
  61 GGGGCTTCCC TGTGCCGCGC GGGGGGCGCC CTCCTCAACA GCAGCGGTGC GGGCAATCTC  120
 121 AGCTGCGAGC CGCCTCGCCT CCGCGGAGCC GGGACACGAG AATTGGAGCT GGCCATTAGG  180
 181 GTCACCCTTT ATGCAGTGAT CTTTCTGATG AGTGTTGGAG GAAATGTGCT CATCATCGTG  240
 241 GTCCTGGGAC TGAGTCGCCG GCTGAGGACT GTCACCAACG CCTTCCTGCT CTCACTGGCA  300
 301 CTCAGCGACC TCCTGCTGGC TGTGGCTTGC ATGCCCTTCA CCCTCCTGCC GAATCTCATG  360
 361 GGCACGTTCA TCTTTGGCAC AGTCGTCTGT AAGGCAGTTT CCTACCTCAT GGGGGTGTCT  420
 421 GTGAGTGTGT CCACACTAAG CCTTGTGGCC ATCGCCCTGG AGCGATACAG CGCCATCTGC  480
 481 CGGCCGCTAC AAGCACGCGT GTGGCAGACG CGTTCCCATG CGGCTCGTGT GATCATCGCC  540
 541 ACTTGGATGC TCTCTGGACT GCTCATGGTG CCCTACCCGG TGTACACCGC CGTACAGCCC  600
 601 GCAGGAGGGG CCCGGGCGCT GCAGTGGGTG CATCGTTGGC CCAGTGCGCG TGTCCGCCAA  660
 661 ACCTGGTCGG TACTGCTGCT CCTGCTTTTG TTCTTCGTCC CAGGCGTGGT TATGGCTGTG  720
 721 GCCTACGGGC TCATCTCCCG CGAGCTCTAC TTAGGGCTTC GCTTCGACGA GGACAGCGAC  780
 781 AGCGAAAGCC GAGTCCGAAG CCAAGGAGGG CTGCGGGGTG GGGCGGGACC AGGTCCTGCC  840
 841 CCCCCAATG GGAGTTGCCG GCCGGAGGGC GGGCTGGCTG GCGAGGACGG CGACGGCTGC  900
 901 TACGTGCAGC TTCCGCGCTC GCGTGAGACC CTGGAGCTGT CCGCGCTGAC CGCGCCCACT  960
 961 CCTGGGCCCG GAGGTGGCCC CCGGCCCTAC CAGGCCAAGC TACGTGCAGC TTCCGCGCTC 1020
1021 GCGTCAGACC CTGGAGCTGT CCGCGCTGAC CGCGCCCACT CCTGGGCCCG GAGGTGGCCC 1080
1081 CCGGCCCTAC GAGGCCAAGC TGTTGGCCAA GAAGCGCGTG GTGCGGATGC TGCTGGTGAT 1140
1141 CGTCGTGCTT TTTTTCCTGT GTTGGTTGCC ACTGTATAGT GCCAACACGT GGCGTGCCTT 1200
1201 TCCACTTGCT GAGCTACGCC TCAGCCTGCG TCAACCCCCT GGTCTACTGC TTCATGCACC 1260
1261 GTCGCTTCCG CCAGGCCTGC CTTGAGACGT GTGCCCGCTG CTGCCCCAGG CCTCCACGAG 1320
1321 CTCGCCCCCG GCCCCTTCCA GACGAGGACC CTCCCACCCC TTCCATTGCT TCACTGTCCA 1380
1381 GACTGAGCTA CACCACCATC AGCACGCTAG GGCCTGGCTG AGGGGTAGGG GGAGAGTGGA 1440
1441 GGCTGAGACG GGACACACCC ATTCCTACAG GCAGGGACCC ACCCAGACAC 1490
```

FIG. 7

HUMAN CCK-B RECEPTOR NECLOTIDE SEQUENCE (CLONE HBR1)

1 GGGCGTTGCC GGCCTGAGAC TGGCGCGGTT GGCGAAGACA

GCGATGGCTG CTACGTGCAA CTTCCA 66

FIG. 8a

COMPARISON OF AMINO ACID SEQUENCE

HUMAN CCK- RECEPTOR          1 GRCRPETGAVGEDSDGCYVQLP 22
                               |.||||.| .|||:||||||||
CANINE GASTRIN RECEPTOR   281 GSCRPEGGLAGEDGDGCYVQLP 302

FIG. 8b

HUMAN CCK-B RECEPTOR Nucleotide Sequence

```
   1 ATGGAGCTGC TAAAGCTGAA CCGGAGCGTG CAGGGAACCg gACCCGGgcc
  51 gggggCttCC CTGTGCCGCc CggggGCgcc TCTCCTCAAC AGCAGCAGTG
 101 TGGGCAACCT CAGCTGCGAG CCCCctcgca ttCgcgGAGC CgggACACgA
 151 GAATTGGAGC TGGCCATTAG AATCACTCTT TACGcaGTGA TCTTccTGAT
 201 GAGCGTTGGA GGAAATATGC TCATCATCGT GGTCCTGGGA CTGAGCCGCC
 251 GCCtGAGGAC TGTCACCAAT GCCTTCCTCC TCTCACTGGC AGTCAGCGAC
 301 CTCCTGCTGG CTGTGGCTTG CATGcccttC ACCCTccTGC CCAATCTCAT
 351 GGGcACATTC ATCTTtggca ccgtcatctg caaggcggtt tcctacctca
 401 tgggggtgtc tgtgagTGTG TCCACGCTAA GCCTCGTGGC CATCGCACTG
 451 GAGCGGTACA GCGCCATCTG CCGACCACTG CAGGCACGAG TGTGGCAGAC
 501 GCGCTCCCAC GCggCTCgcg tgaTTGTAGC CACGTGGCTG CTGTCCGGAC
 551 TACTCATGGT GCcCTACCCC GTGTACACTG TcGTGCAACC AGTGGGGCCT
 601 CGTGTGCTGC AgTGCGTGCA TCgCTGGCCC AGTGCGCGGG TccgccAGAC
 651 CTGGTCCGTA CTGCTGCTTC TGCTCTTGTT CTTCATCCCG GGTGTGGTTA
 701 tggccgtggc cTACGGGCTT ATCTCTCGCG AGCTCTACTT AGGGCTTCGC
 751 TTTGACGGCG ACAGTGACAG CGACAGCCAA AGCAGGGTCC GAAACCAAGG
 801 CGGGCTGCCA GGGGCTGTTC ACCAGAAcGG GCGTTGCCGG CCTGAGACTG
 851 GCGCGGTTGG CGAAGACAGC GATGGCTGCT ACGTGCAACT TCCACGTTCC
 901 CGGCCTGCCC TGGAGCTGAc ggcgcTGACG GCTCCTGGGC CGGGATCCGG
 951 cTCCCGGCCC ACCCAGGCCA AGCTGCTGGC TAAGAAGCGC GTGGTGCGAA
1001 TGTTGCTGGT GATCGTTGTG CTTTTTTTTC TGTGTTGGTT GCCAGTTTAT
1051 AGTGCCAACA CGTGGCGCGC CTTTGATGGC CCGGGTGCAC ACCGAGCACT
1101 CTCGGGTGCT CCTATCTCCT TCATTCACTT GCTGAGCTAC GCCTCGGCCT
1151 GTGTCAACCC CCTGGTCtAC TGCTTCATGC ACcGTcGCTT TcGCCAGGCC
1201 TGCCTGGAAA CTTGCGCTCG CTGCTGCCCC CGGCCTCCAC GAGCTCGCCC
1251 CAGGGcTCTT cCCGATGAGG ACCCTCCCAC TCCcTCCATT GCTTcGcTGT
1301 cCAGGCTTAG CTACACCACC ATCAGCACaC TGGGCCCTGG CTGAGGAGTA
1351 GAGGGG
```

Human Brain Cholecystokinin Receptor Amino Acid Sequence
Deduced from the cDNA

```
  1    MELLKLNRSV   QGTGPGPGAS   LCRPGAPLLN   SSSVGNLSCE   PPRIRGAGTR

51    ELELAIRITL   YAVIFLMSVG   GNMLIIVVLG   LSRRLRTVTN   AFLLSLAVSD

101    LLLAVACMPF   TLLPNLMGTF   IFGTVICKAV   SYLMGVSVSV   STLSLVAIAL

151    ERYSAICRPL   QARVWQTRSH   AARVIVATWL   LSGLLMVPYP   VYTVVQPVGP

201    RVLQCVHRWP   SARVRQTWSV   LLLLLLFFIP   GVVMAVAYGL   ISRELYLGLR

251    FDGDSDSDSQ   SRVRNQGGLP   GAVHQNGRCR   PETGAVGEDS   DGCYVQLPRS

301    RPALELTALT   APGPGSGSRP   TQAKLLAKKR   VVRMLLVIVV   LFFLCWLPVY

351    SANTWRAFDG   PGAHRALSGA   PISFIHLLSY   ASACVNPLVY   CFMHRRFRQA

401    CLETCARCCP   RPPRARPRAL   PDEDPPTPSI   ASLSRLSYTT   ISTLGPG*
```

FIG. 11A

```
         241
hCCK-B     ISRELYLGLRFDGDSDSQSHVRNQGGL....PGAVHQNGRCAPETGA     285
dGASTRIN   ISRELYLGLRFDEDSDSE.SRVASQGGLRQGAGPAPPNGSCRPEGGL
rCCK-A                 SLELYQGIKFDASQKKSAKEKKPSTGS.........ST 286                                                  330
hCCK-B     VGEDSDGCYVQLPRSRPALELTALA..PGPGSG...SRPTQAKLLAKKR
dGASTRIN   AGEDGDGCYVQLPRSRQTELSALTAPTPGPGGG...PRPYQAKLLAKKR
rCCK-A     RYEDSDGCYLQKSRPPRKLELQQLSSGSGGSRLNRIRSSSAANLIAKKR

331            VI                                     380
hCCK-B     VVRMLLVVVLFFLCWLPVYSANTWRAFDGPGAHRALSGAPISFIHLLSY
dGASTRIN   VVRMLLVVVLFFLCWLPLYSANTWRAFDSSGAHRALSGAPISFIHLLSY
rCCK-A     VIRMLIVVVLFFLCWMPIFSANAWRAYDTVSAEKHLSGTPISFILLLSY

381      VII                                           430
hCCK-B     ASACVNPLVYCFMHRRFRQACLETCARCCPRPPRARPRALPDEDPPTPSI
dGASTRIN   ASACVNPLVYCFMHRRFRQACLETCARCCPRPPRARPRPLPDEDPPTPSI
rCCK-A     TSSCVNPITYCFMNKRFRLGFMAIFPCCPNPGPPGVRGEVGEEEDGATIR 431                   447
hCCK-B     ASLSRLSYTTISTLGPG.
dGASTRIN   ASLSRLSYTTISTLGPG.
rCCK-A     ALLSRYSYSHMSTSAPPP
```

FIG. 11B

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 1440
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
GCCGGGGCC                                                                                     9

ATG GAG CTG CTA AAG CTG AAC CGG AGC GCG CAG GGG TCC GGA GCC GGG                              57
Met Glu Leu Leu Lys Leu Asn Arg Ser Ala Gln Gly Ser Gly Ala Gly
1               5                   10                  15

CCG GGG GCT TCC CTG TGC CGC GCG GGG GGC GCC CTC CTC AAC AGC AGC                             105
Pro Gly Ala Ser Leu Cys Arg Ala Gly Gly Ala Leu Leu Asn Ser Ser
            20                  25                  30

GGT GCG GGC AAT CTC AGC TGC GAG CCG CCT CGC CTC CGC GGA GCC GGG                             153
Gly Ala Gly Asn Leu Ser Cys Glu Pro Pro Arg Leu Arg Gly Ala Gly
        35                  40                  45

ACA CGA GAA TTG GAG CTG GCC ATT AGG GTC ACC CTT TAT GCA GTG ATC                             201
Thr Arg Glu Leu Glu Leu Ala Ile Arg Val Thr Leu Tyr Ala Val Ile
    50                  55                  60

TTT CTG ATG AGT GTT GGA GGA AAT GTG CTC ATC ATC GTG GTC CTG GGA                             249
Phe Leu Met Ser Val Gly Gly Asn Val Leu Ile Ile Val Val Leu Gly
65              70                  75                  80

CTG AGT CGC CGG CTG AGG ACT GTC ACC AAC GCC TTC CTG CTC TCA CTG                             297
Leu Ser Arg Arg Leu Arg Thr Val Thr Asn Ala Phe Leu Leu Ser Leu
            85                  90                  95

GCA GTC AGC GAC CTC CTG CTG GCT GTG GCT TGC ATG CCC TTC ACC CTC                             345
Ala Val Ser Asp Leu Leu Leu Ala Val Ala Cys Met Pro Phe Thr Leu
        100                 105                 110

CTG CCC AAT CTC ATG GGC ACG TTC ATC TTT GGC ACA GTC GTC TGT AAG                             393
Leu Pro Asn Leu Met Gly Thr Phe Ile Phe Gly Thr Val Val Cys Lys
    115                 120                 125

GCA GTT TCC TAC CTC ATG GGG GTG TCT GTG AGT GTG TCC ACA CTA AGC                             441
Ala Val Ser Tyr Leu Met Gly Val Ser Val Ser Val Ser Thr Leu Ser
130                 135                 140

CTT GTG GCC ATC GCC CTG GAG CGA TAC AGC GCC ATC TGC CGG CCG CTA                             489
Leu Val Ala Ile Ala Leu Glu Arg Tyr Ser Ala Ile Cys Arg Pro Leu
145                 150                 155                 160

CAA GCA CGC GTG TGG CAG ACG CGT TCC CAT GCG GCT CGT GTG ATC ATC                             537
Gln Ala Arg Val Trp Gln Thr Arg Ser His Ala Ala Arg Val Ile Ile
            165                 170                 175

GCC ACT TGG ATG CTC TCT GGA CTG CTC ATG GTG CCC TAC CCG GTG TAC                             585
Ala Thr Trp Met Leu Ser Gly Leu Leu Met Val Pro Tyr Pro Val Tyr
        180                 185                 190

ACC GCC GTA CAG CCC GCA GGA GGG GCC CGG GCG CTG CAG TGC GTG CAT                             633
Thr Ala Val Gln Pro Ala Gly Gly Ala Arg Ala Leu Gln Cys Val His
    195                 200                 205

CGT TGG CCC AGT GCG CGT GTC CGC CAA ACC TGG TCG GTA CTG CTG CTC                             681
Arg Trp Pro Ser Ala Arg Val Arg Gln Thr Trp Ser Val Leu Leu Leu
210                 215                 220

CTG CTT TTG TTC TTC GTC CCA GGC GTG GTT ATG GCT GTG GCC TAC GGG                             729
Leu Leu Phe Phe Val Pro Gly Val Val Met Ala Val Ala Tyr Gly
225                 230                 235                 240

CTC ATC TCC CGC GAG CTC TAC TTA GGG CTT CGC TTC GAC GAG AAC AGC                             777
Leu Ile Ser Arg Glu Leu Tyr Leu Gly Leu Arg Phe Asp Glu Asn Ser
            245                 250                 255

GAC AGC GAA AGC CGA GTC CGA AGC CAA GGA GGG CTG CGG GGT GGG GCG                             825
Asp Ser Glu Ser Arg Val Arg Ser Gln Gly Gly Leu Arg Gly Gly Ala
        260                 265                 270

GGA CCA GGT CCT GCC CCC CCC AAT GGG AGT TGC CGG CCG GAG GGC GGG                             873
Gly Pro Gly Pro Ala Pro Pro Asn Gly Ser Cys Arg Pro Glu Gly Gly
    275                 280                 285

CTG GCT GGC GAG GAC GGC GAC GGC TGC TAC GTG CAG CTT CCG CGC TCG                             921
Leu Ala Gly Glu Asp Gly Asp Gly Cys Tyr Val Gln Leu Pro Arg Ser
290                 295                 300

CGT CAG ACC CTG GAG CTG TCC GCG CTG ACC GCG CCC ACT CCT GGG CCC                             969
Arg Gln Thr Leu Glu Leu Ser Ala Leu Thr Ala Pro Thr Pro Gly Pro
```

```
                     305                      310                       315                       320
GGA  GGT  GGC  CCC   CGG  CCC  TAC  CAG   GCC  AAG  CTG  TTG   GCC  AAG  AAG  CGC       1017
Gly  Gly  Gly  Pro   Arg  Pro  Tyr  Gln   Ala  Lys  Leu  Leu   Ala  Lys  Lys  Arg
               325                   330                       335

GTG  GTG  CGG  ATG   CTG  CTG  GTG  ATC   GTC  GTG  CTT  TTT   TTC  CTG  TGT  TGG       1065
Val  Val  Arg  Met   Leu  Leu  Val  Ile   Val  Val  Leu  Phe   Phe  Leu  Cys  Trp
               340                   345                       350

TTG  CCA  CTG  TAT   AGT  GCC  AAC  ACG   TGG  CGT  GCC  TTC   GAC  AGC  TCT  GGT       1113
Leu  Pro  Leu  Tyr   Ser  Ala  Asn  Thr   Trp  Arg  Ala  Phe   Asp  Ser  Ser  Gly
               355                   360                       365

GCA  CAC  CGC  GCA   CTT  TCA  GGA  GCG   CCA  ATC  TCT  TTC   ATC  CAC  TTG  CTG       1161
Ala  His  Arg  Ala   Leu  Ser  Gly  Ala   Pro  Ile  Ser  Phe   Ile  His  Leu  Leu
          370                   375                       380

AGC  TAC  GCC  TCA   GCC  TGC  GTC  AAC   CCC  CTG  GTC  TAC   TGC  TTC  ATG  CAC       1209
Ser  Tyr  Ala  Ser   Ala  Cys  Val  Asn   Pro  Leu  Val  Tyr   Cys  Phe  Met  His
385                       390                       395                       400

CGT  CGC  TTC  CGC   CAG  GCC  TGC  CTT   GAG  ACG  TGT  GCC   CGC  TGC  TGC  CCC       1257
Arg  Arg  Phe  Arg   Gln  Ala  Cys  Leu   Glu  Thr  Cys  Ala   Arg  Cys  Cys  Pro
               405                   410                       415

AGG  CCT  CCA  CGA   GCT  CGC  CCC  CGG   CCC  CTT  CCA  GAC   GAG  GAC  CCT  CCC       1305
Arg  Pro  Pro  Arg   Ala  Arg  Pro  Arg   Pro  Leu  Pro  Asp   Glu  Asp  Pro  Pro
               420                   425                       430

ACC  CCT  TCC  ATT   GCT  TCA  CTG  TCC   AGA  CTG  AGC  TAC   ACC  ACC  ATC  AGC       1353
Thr  Pro  Ser  Ile   Ala  Ser  Leu  Ser   Arg  Leu  Ser  Tyr   Thr  Thr  Ile  Ser
               435                   440                       445

ACG  CTA  GGG  CCT  GGC   TGAGGGGTA  GGGGGAGAGT  GGAGGCTGA  GACGGGACA                   1405
Thr  Leu  Gly  Pro  Gly
          450

CACCCATTC  CTACAGGCA  GGGACCCAC  CCAGACAC                                               1440
```

( 2 ) INFORMATION FOR SEQ ID NO: 2:

( i ) SEQUENCE CHARACTERISTICS:
        ( A ) LENGTH: 66
        ( B ) TYPE: nucleic acid
        ( C ) STRANDEDNESS: double
        ( D ) TOPOLOGY: linear ( x i ) SEQUENCE DESCRIPTION: SEQ ID NO: 2:

```
GGG  CGT  TGC  CGG   CCT  GAG  ACT  GGC   GCG  GTT  GGC  GAA   GAC  AGC  GAT  GGC       48
Gly  Arg  Cys  Arg   Pro  Glu  Thr  Gly   Ala  Val  Gly  Glu   Asp  Ser  Asp  Gly
1                5                     10                     15

TGC  TAC  GTG  CAA  CTT  CCA                                                             66
Cys  Tyr  Val  Gln  Leu  Pro
               20
```

( 2 ) INFORMATION FOR SEQ ID NO: 3:

( i ) SEQUENCE CHARACTERISTICS:
        ( A ) LENGTH: 22
        ( B ) TYPE: amino acid
        ( C ) STRANDEDNESS:
        ( D ) TOPOLOGY: linear ( x i ) SEQUENCE DESCRIPTION: SEQ ID NO: 3:

```
Gly  Ser  Cys  Arg   Pro  Glu  Gly  Gly   Leu  Ala  Gly  Glu   Asp  Gly  Asp  Gly
1                5                     10                     15

Cys  Tyr  Val  Gln  Leu  Pro
               20
```

( 2 ) INFORMATION FOR SEQ ID NO: 4:

( i ) SEQUENCE CHARACTERISTICS:

5,541,071

-continued ( A ) LENGTH: 1356
( B ) TYPE: nucleic acid
( C ) STRANDEDNESS: double
( D ) TOPOLOGY: linear ( x i ) SEQUENCE DESCRIPTION: SEQ ID NO: 4:

```
ATG GAG CTG CTA AAG CTG AAC CGG AGC GTG CAG GGA ACC GGA CCC GGG    48
Met Glu Leu Leu Lys Leu Asn Arg Ser Val Gln Gly Thr Gly Pro Gly
 1               5                  10                  15

CCG GGG GCT TCC CTG TGC CGC CCG GGG GCG CCT CTC CTC AAC AGC AGC    96
Pro Gly Ala Ser Leu Cys Arg Pro Gly Ala Pro Leu Leu Asn Ser Ser
                20                  25                  30

AGT GTG GGC AAC CTC AGC TGC GAG CCC CCT CGC ATT CGC GGA GCC GGG   144
Ser Val Gly Asn Leu Ser Cys Glu Pro Pro Arg Ile Arg Gly Ala Gly
             35                  40                  45

ACA CGA GAA TTG GAG CTG GCC ATT AGA ATC ACT CTT TAC GCA GTG ATC   192
Thr Arg Glu Leu Glu Leu Ala Ile Arg Ile Thr Leu Tyr Ala Val Ile
         50                  55                  60

TTC CTG ATG AGC GTT GGA GGA AAT ATG CTC ATC ATC GTG GTC CTG GGA   240
Phe Leu Met Ser Val Gly Gly Asn Met Leu Ile Ile Val Val Leu Gly
 65                  70                  75                  80

CTG AGC CGC CGC CTG AGG ACT GTC ACC AAT GCC TTC CTC CTC TCA CTG   288
Leu Ser Arg Arg Leu Arg Thr Val Thr Asn Ala Phe Leu Leu Ser Leu
                 85                  90                  95

GCA GTC AGC GAC CTC CTG CTG GCT GTG GCT TGC ATG CCC TTC ACC CTC   336
Ala Val Ser Asp Leu Leu Leu Ala Val Ala Cys Met Pro Phe Thr Leu
                100                 105                 110

CTG CCC AAT CTC ATG GGC ACA TTC ATC TTT GGC ACC GTC ATC TGC AAG   384
Leu Pro Asn Leu Met Gly Thr Phe Ile Phe Gly Thr Val Ile Cys Lys
            115                 120                 125

GCG GTT TCC TAC CTC ATG GGG GTG TCT GTG AGT GTG TCC ACG CTA AGC   432
Ala Val Ser Tyr Leu Met Gly Val Ser Val Ser Val Ser Thr Leu Ser
        130                 135                 140

CTC GTG GCC ATC GCA CTG GAG CGG TAC AGC GCC ATC TGC CGA CCA CTG   480
Leu Val Ala Ile Ala Leu Glu Arg Tyr Ser Ala Ile Cys Arg Pro Leu
145                 150                 155                 160

CAG GCA CGA GTG TGG CAG ACG CGC TCC CAC GCG GCT CGC GTG ATT GTA   528
Gln Ala Arg Val Trp Gln Thr Arg Ser His Ala Ala Arg Val Ile Val
                165                 170                 175

GCC ACG TGG CTG CTG TCC GGA CTA CTC ATG GTG CCC TAC CCC GTG TAC   576
Ala Thr Trp Leu Leu Ser Gly Leu Leu Met Val Pro Tyr Pro Val Tyr
            180                 185                 190

ACT GTC GTG CAA CCA GTG GGG CCT CGT GTG CTG CAG TGC GTG CAT CGC   624
Thr Val Val Gln Pro Val Gly Pro Arg Val Leu Gln Cys Val His Arg
        195                 200                 205

TGG CCC AGT GCG CGG GTC CGC CAG ACC TGG TCC GTA CTG CTG CTT CTG   672
Trp Pro Ser Ala Arg Val Arg Gln Thr Trp Ser Val Leu Leu Leu Leu
210                 215                 220

CTC TTG TTC TTC ATC CCG GGT GTG GTT ATG GCC GTG GCC TAC GGG CTT   720
Leu Leu Phe Phe Ile Pro Gly Val Val Met Ala Val Ala Tyr Gly Leu
225                 230                 235                 240

ATC TCT CGC GAG CTC TAC TTA GGG CTT CGC TTT GAC GGC GAC AGT GAC   768
Ile Ser Arg Glu Leu Tyr Leu Gly Leu Arg Phe Asp Gly Asp Ser Asp
                245                 250                 255

AGC GAC AGC CAA AGC AGG GTC CGA AAC CAA GGC GGG CTG CCA GGG GCT   816
Ser Asp Ser Gln Ser Arg Val Arg Asn Gln Gly Gly Leu Pro Gly Ala
            260                 265                 270

GTT CAC CAG AAC GGG CGT TGC CGG CCT GAG ACT GGC GCG GTT GGC GAA   864
Val His Gln Asn Gly Arg Cys Arg Pro Glu Thr Gly Ala Val Gly Glu
        275                 280                 285

GAC AGC GAT GGC TGC TAC GTG CAA CTT CCA CGT TCC CGG CCT GCC CTG   912
```

|   |   |   |   |   |   |   |   |   |   |   |   |   |   |   |   |   |
|---|---|---|---|---|---|---|---|---|---|---|---|---|---|---|---|---|
| Asp | Ser | Asp | Gly | Cys | Tyr | Val | Gln | Leu | Pro | Arg | Ser | Arg | Pro | Ala | Leu | |
|     | 290 |     |     |     | 295 |     |     |     |     | 300 |     |     |     |     |     | |

| GAG | CTG | ACG | GCG | CTG | ACG | GCT | CCT | GGG | CCG | GGA | TCC | GGC | TCC | CGG | CCC | 960 |
|-----|-----|-----|-----|-----|-----|-----|-----|-----|-----|-----|-----|-----|-----|-----|-----|-----|
| Glu | Leu | Thr | Ala | Leu | Thr | Ala | Pro | Gly | Pro | Gly | Ser | Gly | Ser | Arg | Pro |     |
| 305 |     |     |     |     | 310 |     |     |     |     | 315 |     |     |     |     | 320 |     |

| ACC | CAG | GCC | AAG | CTG | CTG | GCT | AAG | AAG | CGC | GTG | GTG | CGA | ATG | TTG | CTG | 1008 |
|-----|-----|-----|-----|-----|-----|-----|-----|-----|-----|-----|-----|-----|-----|-----|-----|------|
| Thr | Gln | Ala | Lys | Leu | Leu | Ala | Lys | Lys | Arg | Val | Val | Arg | Met | Leu | Leu |      |
|     |     |     |     | 325 |     |     |     |     | 330 |     |     |     |     | 335 |     |      |

| GTG | ATC | GTT | GTG | CTT | TTT | TTT | CTG | TGT | TGG | TTG | CCA | GTT | TAT | AGT | GCC | 1056 |
|-----|-----|-----|-----|-----|-----|-----|-----|-----|-----|-----|-----|-----|-----|-----|-----|------|
| Val | Ile | Val | Val | Leu | Phe | Phe | Leu | Cys | Trp | Leu | Pro | Val | Tyr | Ser | Ala |      |
|     |     |     | 340 |     |     |     |     | 345 |     |     |     |     | 350 |     |     |      |

| AAC | ACG | TGG | CGC | GCC | TTT | GAT | GGC | CCG | GGT | GCA | CAC | CGA | GCA | CTC | TCG | 1104 |
|-----|-----|-----|-----|-----|-----|-----|-----|-----|-----|-----|-----|-----|-----|-----|-----|------|
| Asn | Thr | Trp | Arg | Ala | Phe | Asp | Gly | Pro | Gly | Ala | His | Arg | Ala | Leu | Ser |      |
|     |     | 355 |     |     |     |     | 360 |     |     |     |     | 365 |     |     |     |      |

| GGT | GCT | CCT | ATC | TCC | TTC | ATT | CAC | TTG | CTG | AGC | TAC | GCC | TCG | GCC | TGT | 1152 |
|-----|-----|-----|-----|-----|-----|-----|-----|-----|-----|-----|-----|-----|-----|-----|-----|------|
| Gly | Ala | Pro | Ile | Ser | Phe | Ile | His | Leu | Leu | Ser | Tyr | Ala | Ser | Ala | Cys |      |
| 370 |     |     |     |     |     | 375 |     |     |     |     | 380 |     |     |     |     |      |

| GTC | AAC | CCC | CTG | GTC | TAC | TGC | TTC | ATG | CAC | CGT | CGC | TTT | CGC | CAG | GCC | 1200 |
|-----|-----|-----|-----|-----|-----|-----|-----|-----|-----|-----|-----|-----|-----|-----|-----|------|
| Val | Asn | Pro | Leu | Val | Tyr | Cys | Phe | Met | His | Arg | Arg | Phe | Arg | Gln | Ala |      |
| 385 |     |     |     |     | 390 |     |     |     | 395 |     |     |     |     |     | 400 |      |

| TGC | CTG | GAA | ACT | TGC | GCT | CGC | TGC | TGC | CCC | CGG | CCT | CCA | CGA | GCT | CGC | 1248 |
|-----|-----|-----|-----|-----|-----|-----|-----|-----|-----|-----|-----|-----|-----|-----|-----|------|
| Cys | Leu | Glu | Thr | Cys | Ala | Arg | Cys | Cys | Pro | Arg | Pro | Pro | Arg | Ala | Arg |      |
|     |     |     |     | 405 |     |     |     |     | 410 |     |     |     |     | 415 |     |      |

| CCC | AGG | GCT | CTT | CCC | GAT | GAG | GAC | CCT | CCC | ACT | CCC | TCC | ATT | GCT | TCG | 1296 |
|-----|-----|-----|-----|-----|-----|-----|-----|-----|-----|-----|-----|-----|-----|-----|-----|------|
| Pro | Arg | Ala | Leu | Pro | Asp | Glu | Asp | Pro | Pro | Thr | Pro | Ser | Ile | Ala | Ser |      |
|     |     |     | 420 |     |     |     |     | 425 |     |     |     |     | 430 |     |     |      |

| CTG | TCC | AGG | CTT | AGC | TAC | ACC | ACC | ATC | AGC | ACA | CTG | GGC | CCT | GGC | TGA | 1344 |
|-----|-----|-----|-----|-----|-----|-----|-----|-----|-----|-----|-----|-----|-----|-----|-----|------|
| Leu | Ser | Arg | Leu | Ser | Tyr | Thr | Thr | Ile | Ser | Thr | Leu | Gly | Pro | Gly |     |      |
|     |     | 435 |     |     |     |     | 440 |     |     |     |     | 445 |     |     |     |      |

| GGA | GTA | GAG | GGG | | | | | | | | | | | | | 1356 |
|-----|-----|-----|-----|-|-|-|-|-|-|-|-|-|-|-|-|------|
|     | 450 |     |     | | | | | | | | | | | | |      |

( 2 ) INFORMATION FOR SEQ ID NO:5:

( i ) SEQUENCE CHARACTERISTICS:
        ( A ) LENGTH: 453 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:5:

| Met | Glu | Leu | Leu | Lys | Leu | Asn | Arg | Ser | Ala | Gln | Gly | Ser | Gly | Ala | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Gly | Ala | Ser | Leu | Cys | Arg | Ala | Gly | Gly | Ala | Leu | Leu | Asn | Ser | Ser |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gly | Ala | Gly | Asn | Leu | Ser | Cys | Glu | Pro | Pro | Arg | Leu | Arg | Gly | Ala | Gly |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Arg | Glu | Leu | Glu | Leu | Ala | Ile | Arg | Val | Thr | Leu | Tyr | Ala | Val | Ile |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Phe | Leu | Met | Ser | Val | Gly | Gly | Asn | Val | Leu | Ile | Ile | Val | Val | Leu | Gly |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Leu | Ser | Arg | Arg | Leu | Arg | Thr | Val | Thr | Asn | Ala | Phe | Leu | Leu | Ser | Leu |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ala | Val | Ser | Asp | Leu | Leu | Leu | Ala | Val | Ala | Cys | Met | Pro | Phe | Thr | Leu |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Leu | Pro | Asn | Leu | Met | Gly | Thr | Phe | Ile | Phe | Gly | Thr | Val | Val | Cys | Lys |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ala | Val | Ser | Tyr | Leu | Met | Gly | Val | Ser | Val | Ser | Val | Ser | Thr | Leu | Ser |
|-----|-----|-----|-----|-----|-----|-----|-----|-----|-----|-----|-----|-----|-----|-----|-----|

|   |   |   |   | 130 |   |   |   |   | 135 |   |   |   |   | 140 |   |   |   |
|---|---|---|---|---|---|---|---|---|---|---|---|---|---|---|---|---|---|
| Leu | Val | Ala | Ile | Ala | Leu | Glu | Arg | Tyr | Ser | Ala | Ile | Cys | Arg | Pro | Leu |
| 145 |   |   |   | 150 |   |   |   |   | 155 |   |   |   |   |   | 160 |
| Gln | Ala | Arg | Val | Trp | Gln | Thr | Arg | Ser | His | Ala | Ala | Arg | Val | Ile | Ile |
|   |   |   |   | 165 |   |   |   |   | 170 |   |   |   |   | 175 |   |
| Ala | Thr | Trp | Met | Leu | Ser | Gly | Leu | Leu | Met | Val | Pro | Tyr | Pro | Val | Tyr |
|   |   |   | 180 |   |   |   |   | 185 |   |   |   |   | 190 |   |   |
| Thr | Ala | Val | Gln | Pro | Ala | Gly | Ala | Arg | Ala | Leu | Gln | Cys | Val | His |
|   |   | 195 |   |   |   | 200 |   |   |   |   | 205 |   |   |   |
| Arg | Trp | Pro | Ser | Ala | Arg | Val | Arg | Gln | Thr | Trp | Ser | Val | Leu | Leu | Leu |
|   | 210 |   |   |   |   | 215 |   |   |   |   | 220 |   |   |   |   |
| Leu | Leu | Leu | Phe | Phe | Val | Pro | Gly | Val | Val | Met | Ala | Val | Ala | Tyr | Gly |
| 225 |   |   |   |   | 230 |   |   |   |   | 235 |   |   |   |   | 240 |
| Leu | Ile | Ser | Arg | Glu | Leu | Tyr | Leu | Gly | Leu | Arg | Phe | Asp | Glu | Asp | Ser |
|   |   |   |   | 245 |   |   |   |   | 250 |   |   |   |   | 255 |   |
| Asp | Ser | Glu | Ser | Arg | Val | Arg | Ser | Gln | Gly | Gly | Leu | Arg | Gly | Gly | Ala |
|   |   |   | 260 |   |   |   |   | 265 |   |   |   |   | 270 |   |   |
| Gly | Pro | Gly | Pro | Ala | Pro | Pro | Asn | Gly | Ser | Cys | Arg | Pro | Glu | Gly | Gly |
|   |   | 275 |   |   |   |   | 280 |   |   |   |   | 285 |   |   |   |
| Leu | Ala | Gly | Glu | Asp | Gly | Asp | Gly | Cys | Tyr | Val | Gln | Leu | Pro | Arg | Ser |
|   | 290 |   |   |   |   | 295 |   |   |   |   | 300 |   |   |   |   |
| Arg | Gln | Thr | Leu | Glu | Leu | Ser | Ala | Leu | Thr | Ala | Pro | Thr | Pro | Gly | Pro |
| 305 |   |   |   |   | 310 |   |   |   |   | 315 |   |   |   |   | 320 |
| Gly | Gly | Gly | Pro | Arg | Pro | Tyr | Gln | Ala | Lys | Leu | Leu | Ala | Lys | Lys | Arg |
|   |   |   |   | 325 |   |   |   |   | 330 |   |   |   |   | 335 |   |
| Val | Val | Arg | Met | Leu | Leu | Val | Ile | Val | Val | Leu | Phe | Phe | Leu | Cys | Trp |
|   |   |   | 340 |   |   |   |   | 345 |   |   |   |   | 350 |   |   |
| Leu | Pro | Leu | Tyr | Ser | Ala | Asn | Thr | Trp | Arg | Ala | Phe | Asp | Ser | Ser | Gly |
|   |   | 355 |   |   |   |   | 360 |   |   |   |   | 365 |   |   |   |
| Ala | His | Arg | Ala | Leu | Ser | Gly | Ala | Pro | Ile | Ser | Phe | Ile | His | Leu | Leu |
|   | 370 |   |   |   |   | 375 |   |   |   |   | 380 |   |   |   |   |
| Ser | Tyr | Ala | Ser | Ala | Cys | Val | Asn | Pro | Leu | Val | Tyr | Cys | Phe | Met | His |
| 385 |   |   |   |   | 390 |   |   |   |   | 395 |   |   |   |   | 400 |
| Arg | Arg | Phe | Arg | Gln | Ala | Cys | Leu | Glu | Thr | Cys | Ala | Arg | Cys | Cys | Pro |
|   |   |   |   | 405 |   |   |   |   | 410 |   |   |   |   | 415 |   |
| Arg | Pro | Pro | Arg | Ala | Arg | Pro | Arg | Pro | Leu | Pro | Asp | Glu | Asp | Pro | Pro |
|   |   |   | 420 |   |   |   |   | 425 |   |   |   |   | 430 |   |   |
| Thr | Pro | Ser | Ile | Ala | Ser | Leu | Ser | Arg | Leu | Ser | Tyr | Thr | Thr | Ile | Ser |
|   |   | 435 |   |   |   |   | 440 |   |   |   |   | 445 |   |   |   |
| Thr | Leu | Gly | Pro | Gly |   |   |   |   |   |   |   |   |   |   |   |
| 450 |   |   |   |   |   |   |   |   |   |   |   |   |   |   |   |

( 2 ) INFORMATION FOR SEQ ID NO:6:

( i ) SEQUENCE CHARACTERISTICS:
        ( A ) LENGTH: 447 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:6:

| Met | Glu | Leu | Leu | Lys | Leu | Asn | Arg | Ser | Val | Gln | Gly | Thr | Gly | Pro | Gly |
|---|---|---|---|---|---|---|---|---|---|---|---|---|---|---|---|
| 1 |   |   |   | 5 |   |   |   |   | 10 |   |   |   |   | 15 |   |
| Pro | Gly | Ala | Ser | Leu | Cys | Arg | Pro | Gly | Ala | Pro | Leu | Leu | Asn | Ser | Ser |
|   |   |   | 20 |   |   |   |   | 25 |   |   |   |   | 30 |   |   |

```
Ser  Val  Gly  Asn  Leu  Ser  Cys  Glu  Pro  Pro  Arg  Ile  Arg  Gly  Ala  Gly
          35                  40                      45

Thr  Arg  Glu  Leu  Glu  Leu  Ala  Ile  Arg  Ile  Thr  Leu  Tyr  Ala  Val  Ile
     50                       55                      60

Phe  Leu  Met  Ser  Val  Gly  Gly  Asn  Met  Leu  Ile  Ile  Val  Val  Leu  Gly
65                       70                       75                           80

Leu  Ser  Arg  Arg  Leu  Arg  Thr  Val  Thr  Asn  Ala  Phe  Leu  Leu  Ser  Leu
               85                            90                      95

Ala  Val  Ser  Asp  Leu  Leu  Ala  Val  Ala  Cys  Met  Pro  Phe  Thr  Leu
               100                 105                      110

Leu  Pro  Asn  Leu  Met  Gly  Thr  Phe  Ile  Phe  Gly  Thr  Val  Ile  Cys  Lys
          115                      120                      125

Ala  Val  Ser  Tyr  Leu  Met  Gly  Val  Ser  Val  Ser  Val  Ser  Thr  Leu  Ser
     130                      135                      140

Leu  Val  Ala  Ile  Ala  Leu  Glu  Arg  Tyr  Ser  Ala  Ile  Cys  Arg  Pro  Leu
145                           150                      155                      160

Gln  Ala  Arg  Val  Trp  Gln  Thr  Arg  Ser  His  Ala  Ala  Arg  Val  Ile  Val
                    165                      170                      175

Ala  Thr  Trp  Leu  Leu  Ser  Gly  Leu  Leu  Met  Val  Pro  Tyr  Pro  Val  Tyr
               180                      185                      190

Thr  Val  Val  Gln  Pro  Val  Gly  Pro  Arg  Val  Leu  Gln  Cys  Val  His  Arg
          195                      200                      205

Trp  Pro  Ser  Ala  Arg  Val  Arg  Gln  Thr  Trp  Ser  Val  Leu  Leu  Leu  Leu
     210                      215                      220

Leu  Leu  Phe  Phe  Ile  Pro  Gly  Val  Val  Met  Ala  Val  Ala  Tyr  Gly  Leu
225                      230                      235                           240

Ile  Ser  Arg  Glu  Leu  Tyr  Leu  Gly  Leu  Arg  Phe  Asp  Gly  Asp  Ser  Asp
                    245                      250                      255

Ser  Asp  Ser  Gln  Ser  Arg  Val  Arg  Asn  Gln  Gly  Gly  Leu  Pro  Gly  Ala
               260                      265                      270

Val  His  Gln  Asn  Gly  Arg  Cys  Arg  Pro  Glu  Thr  Gly  Ala  Val  Gly  Glu
          275                      280                      285

Asp  Ser  Asp  Gly  Cys  Tyr  Val  Gln  Leu  Pro  Arg  Ser  Arg  Pro  Ala  Leu
     290                      295                      300

Glu  Leu  Thr  Ala  Leu  Thr  Ala  Pro  Gly  Pro  Gly  Ser  Gly  Ser  Arg  Pro
305                      310                      315                           320

Thr  Gln  Ala  Lys  Leu  Leu  Ala  Lys  Lys  Arg  Val  Val  Arg  Met  Leu  Leu
               325                      330                      335

Val  Ile  Val  Val  Leu  Phe  Phe  Leu  Cys  Trp  Leu  Pro  Val  Tyr  Ser  Ala
               340                      345                      350

Asn  Thr  Trp  Arg  Ala  Phe  Asp  Gly  Pro  Gly  Ala  His  Arg  Ala  Leu  Ser
               355                      360                      365

Gly  Ala  Pro  Ile  Ser  Phe  Ile  His  Leu  Leu  Ser  Tyr  Ala  Ser  Ala  Cys
     370                      375                      380

Val  Asn  Pro  Leu  Val  Tyr  Cys  Phe  Met  His  Arg  Arg  Phe  Arg  Gln  Ala
385                           390                      395                      400

Cys  Leu  Glu  Thr  Cys  Ala  Arg  Cys  Cys  Pro  Arg  Pro  Pro  Arg  Ala  Arg
               405                      410                      415

Pro  Arg  Ala  Leu  Pro  Asp  Glu  Asp  Pro  Pro  Thr  Pro  Ser  Ile  Ala  Ser
               420                      425                      430

Leu  Ser  Arg  Leu  Ser  Tyr  Thr  Thr  Ile  Ser  Thr  Leu  Gly  Pro  Gly
          435                      440                      445
```

ASSAY FOR IDENTIFYING ANTAGONISTS OF GASTRIN AND CCK-B RECEPTORS

This invention was made with Government support under #DK01934, #P30DK39428, and #DK32878 awarded by the National Institute of Health. The government has certain rights in the invention.

BACKGROUND OF THE INVENTION

This application is a continuation-in-part of Kopin, U.S. Ser. No. 07/941,373, filed Sept. 3, 1992, now abandoned, which is in turn a continuation-in-part of Kopin, U.S. Ser. No. 07/832,841, filed Feb. 7, 1992, now abandoned.

This invention relates to the gastrin/cholecystokinin (CCK-B) family of receptors.

Gastrin is a 17 amino acid peptide hormone produced by gastric antral G cells. The principal physiologic effect of this hormone is the stimulation of gastric parietal cells to secrete hydrochloric acid. Gastrin is also a trophic hormone, modulating growth and differentiation of the gastric mucosa, as well as the mucosa of the small and large intestine, during normal development (Johnson, L. R., 1987, *Physiology of the Gastrointestinal Tract* Raven Press, N.Y.) and in certain pathologic states (e.g. Zollinger-Ellison Syndrome, gastric carcinoma, pernicious anemia). Physiologic effects of this peptide are triggered when gastrin binds to its plasmalemma receptor, tentatively identified by affinity labeling as a protein with an apparent molecular weight of 74,000 daltons (Baldwin, G. S., et al., 1986, *J Biol Chem* 261:12252–7, Matsumoto, M., et al., 1987, *Am J Physiol* 252:G143–G147). Agonist stimulation of gastrin receptors on parietal cells results in phosphatidylinositol hydrolysis and elevation of intracellular calcium concentration (Muallem, S. & Sachs, G., 1984, *Biochim Biophys Acta* 805:181–5, Chew, C. S. & Brown, M. R., 1986, *Biochim Biophys Acta* 888:116–25), mediated through guanine nucleotide-binding proteins (G-proteins) (Roche, S., et al., 1990, *Biochim Biophys Acta* 1055:287–94). Gastrin, cholecystokinin (CCK), and CCK-related peptides comprise a hormone family, characterized by the identical carboxyl-terminal pentapeptide amide structure, a domain critical for receptor binding.

The corresponding target receptors for this hormone family can be divided into two main classes, CCK-A and CCK-B/gastrin receptors, based on their agonist and antagonist specificity patterns (Miller, L. J., 1991, in *CCK antagonists in gastroenterology,* Springer-Verlag, Berlin, p. 27–34). The peripheral or "alimentary" receptor (CCK-A), found on pancreas, gallbladder, and certain brain nuclei, has a 1,000-fold higher affinity for sulphated CCK-8 than for gastrin. CCK-B/gastrin receptors are found in the brain ("CCK-B"), on smooth muscle cells, and on parietal cells ("gastrin" receptors). Binding studies on brain membranes and parietal cells comparing the relative affinities for agonists show a 6–10 fold and a 1–2 fold higher affinity for CCK than for gastrin, respectively (Jensen, R. T. et al., in *Gastrointestinal Endocrinology: Receptors and Post-Receptor Mechanisms,* Harcourt Brace Jovanovich, San Diego, p. 95). Central CCK sites (CCK-B) display a high affinity for the sulphated octapeptide fragment (CCK-8s), the desulphated octapeptide (CCK-8d), gastrin, CCK-4 (the C-terminal tetrapeptide of CCK), and pentagastrin (CCK-5), and resemble gastrin receptors in their agonist selectivity. CCK-B receptors may play a role in anxiety, modulation of pain, memory, satiety, and panic disorders. CCK is the most abundant neuropeptide, and CCK-B is the most abundant receptor subtype, in the brain (CCK-B>>>CCK-A).

SUMMARY OF THE INVENTION

The invention generally features a purified nucleic acid encoding a member of the mammalian gastrin/cholecystokinin (CCK-B) receptor family, or a fragment or analog thereof. By "mammalian gastrin/CCK-B receptor family" is meant polypeptides of mammalian origin that generally exhibit at least 60%, more preferably 80%, more preferably 90%, and most preferably 95% or even 99%, homology with a naturally occurring mammalian gastrin receptor/CCK-B receptor amino acid sequence (shown in FIG. 1; SEQ ID NO: 5; SEQ ID NO: 6). Preferably the nucleic acid encodes a gastrin receptor; the nucleic acid encodes a CCK-B receptor; the member of the gastrin/CCK-B receptor family is found on the surface of parietal cells, brain cells, immunologic cells, entero-chromaffin-like cells (ECL), tumor cells, e.g., colon cancer cells, small cell lung carcinoma cells, or leiomyoma cells, or smooth muscle cells, preferably when those cells are from a canine or, more preferably, when those cells are from a human.

The invention also features a homogeneous population of cells wherein each of the cells contain cloned nucleic acid encoding a member of the mammalian gastrin/CCK-B receptor family. Bacterial cells transfected with the purified nucleic acid encoding the gastrin receptor (clone GR-1) are deposited with the ATCC and designated No. 75195. Two clones of bacterial cells transfected with the purified nucleic acid encoding a portion (HBR-1), or the full-length (hCCKB; FBCR-4), of the CCK-B receptor are deposited with the A.T.C.C. and designated Nos. 75196 and 75303, respectively. Cells containing a nucleic acid of the invention can preferably express a biologically active polypeptide of the gastrin/CCK-B receptor family. The cells can also be eukaryotic cells, e.g., COS-7, or Chinese Hamster Ovary (CHO) cells.

The invention additionally features substantially pure gastrin receptor polypeptide produced from a nucleic acid encoding a member of the mammalian gastrin/CCK-B receptor family, or a fragment or analog thereof. In preferred embodiments, the gastrin receptor polypeptide includes an amino acid sequence substantially identical to the amino acids 1 to 453 of SEQ ID NO: 5.

```
1                                                            60
MELLKLNRSAQGSGAGPGASLCRAGGALLNSSGAGNLSCEPPRLRGAGTRELELAIRVTL 61                                                           120
YAVIFLMSVGGNVLIIVVLGLSRRLRTVTNAFLLSLAVSDLLLAVACMPFTLLPNLMGTF 121                                                          180
IFGTVVCKAVSYLMGVSVSVSTLSLVAIALERYSAICRPLQARVWQTRSHAARVIIATWM 181                                                          240
LSGLLMVPYPVYTAVQPAGGARALQCVHRWPSARVROTWSVLLLLLLFFVPGVVMAVAYG
```

```
241                                                             300
LISRELYLGLRFDEDSDSESRVRSQGGLRGGAGPGPAPPNGSCRPEGGLAGEDGDGCYVQ 301                                                             360
LPRSRQTLELSALTAPTPGPGGGPRPYQAKLLAKKRVVRMLLVIVVLFFLCWLPLYSANT 361                                                             420
WRAFDSSGAHRALSGAPISFIHLLSYASACVNPLVYCFMHRRFRQACLETCARCCPRPPR 421               453
ARPRPLPDEDPPTPSIASLSRLSYTTISTLGPG.
```

In other preferred embodiments, the apparent molecular weight of the glycosylated polypeptide is approximately 76,000 daltons; the polypeptide is glycosylated or unglycosylated; and the polypeptide is expressed by human cells, e.g. human parietal cells, brain cells, smooth muscle cells, immunologic cells, ECL cells, or tumor cells.

The invention also generally includes substantially pure CCK-B receptor polypeptide produced from a nucleic acid encoding a member of the mammalian gastrin/CCK-B receptor family, or a fragment or analog thereof. The CCK-B receptor polypeptide can include an amino acid sequence substantially identical to the amino acids 1 to 447 of the sequence listed in SEQ ID NO: 6.

method involves providing a gastrin/CCK-B receptor family-specific agonist to cultured cells transfected with, for example, the GR-1 cDNA or CCK-B cDNA of the invention in the presence of a candidate antagonist, and determining the ability of the candidate antagonist to either, a) interfere with binding of the agonist to the gastrin receptor, or b) block an agonist-induced increase in free cytosolic calcium $[Ca^{+2}]$, or c) block an agonist-induced activation of phospholipase C, or d) block an agonist-induced activation of adenyl cyclase as an indication of antagonist activity. The agonist can be gastrin, e.g., gastrin-17 or gastrin-34 (sulphated or desulphated) or the agonist can be cholecystokinin (CCK), more preferably CCK-8s, CCK-8d, CCK-4, or

```
1                                                               60
MELLKLNRSVQGTGPGPGASLCRPGAPLLNSSSVGNLSCEPPRIRGAGTRELELAIRITL 61                                                              120
YAVIFLMSVGGNMLIIVVLGLSRRLRTVTNAFLLSLAVSDLLLAVACMPFTLLPNLMGTF 121                                                             180
IFGTVICKAVSYLMGVSVSVSTLSLVAIALERYSAICRPLQARVWQTRSHAARVIVATWL 181                                                             240
LSGLLMVPYPVYTVVQPVGPRVLQCVHRWPSARVRQTWSVLLLLLLFFIPGVVMAVAYGL 241                                                             300
ISRELYLGLRFDGDSDSDSQSRVRNQGGLPGAVHQNGRCRPETGAVGEDSDGCYVQLPRS 301                                                             360
RPALELTALTAPGPGSGSRPTQAKLLAKKRVVRMLLVIVVLFFLCWLPVYSANTWRAFDG 361                                                             420
PGAHRALSGAPISFIHLLSYASACVNPLVYCFMHRRFRQACLETCARCCPRPPRARPRAL 421               447
PDEDPPTPSIASLSRLSYTTISTLGPG.
```

The CCK-B polypeptide can be glycosylated or unglycosylated, and expressed by human cells, e.g. human parietal cells, human brain cells, or human smooth muscle cells.

In another aspect, the invention features a parietal cell cDNA expression library. Preferably the cDNA segments of the library are derived from canine parietal cells, human parietal cells, or human chief cells. The expression vector used in the cDNA library can include one or more of the following: the SV40 replication origin; or the cytomegalovirus (CMV) promoter. More preferably, the cDNA library is constructed with an expression vector comprised of pCDNA-1, or λgt11.

The invention also features a method for isolating nucleic acids encoding polypeptides found in parietal cells, involving screening the cDNA expression library, preferably for an isolated nucleic acid encoding the prostaglandin $E_2$ ($PGE_2$) receptor.

DNA encoding a member of the mammalian gastrin/CCK-B receptor family of the invention can be used in a method for identifying an antagonist to the member. The pentagastrin (CCK-5). Agonist, as used herein, refers to a chemical substance capable of combining with a receptor and initiating an activity of the receptor. As a preferred embodiment, the invention includes an antagonist to a member of the mammalian gastrin/CCK-B receptor family identified according to this method. Antagonist, as used herein, refers to a chemical substance that inhibits an activity of the receptor, such as its ability to bind an agonist.

Glycosylated, as used herein, refers to having one or more covalently-linked carbohydrate moieties attached to the protein. By "unglycosylated" is meant lacking covalently-linked carbohydrate moieties. By "apparent molecular weight" is meant the molecular weight, determined on a denaturing polyacrylamide gel, by comparison with standards, e.g., protein standards, of known molecular weight. "Receptor" as used herein, refers to a molecule on the surface of a target cell that binds to a hormone, e.g. gastrin, or CCK.

"Substantially pure" as used herein, refers to a preparation, e.g., of a protein, that is substantially separated from the proteins, lipids, and other materials with which it is naturally associated. Typically, a compound is substantially pure when at least 10%, more preferably at least 20%, more preferably at least 50%, more preferably at least 60%, more preferably at least 75%, more preferably at least 90%, and most preferably at least 99%, of the total material (by volume, by wet or dry weight, or by mole percent or mole fraction) in a sample is the protein of interest. Purity can be measured by any appropriate method, for instance by column chromatography, polyacrylamide gel electrophoresis, or HPLC analysis. A protein is also substantially purified when it is free of naturally associated components or when it is separated from the native contaminants that accompany it in its natural state.

"Substantially identical amino acid sequence", as used herein, refers to an amino acid sequence that differs only by conservative amino acid substitutions, for example, substitution of one amino acid for another of the same class (e.g., amino acids that share characteristics of hydrophobicity, charge, $pK_a$, or other conformational or chemical properties, e.g., valine for leucine, arginine for lysine, etc.) or by one or more non-conservative amino acid substitutions, deletions, or insertions, located at positions of the amino acid sequence that do not destroy the biological activity of the polypeptide (as described above). An amino acid sequence is included within the scope of the invention if it differs by a modification that reduces or alters the biological activity, or that alters one receptor activity but not another. For example, an alteration that alters ligand binding activity but not the receptor's signalling activity, or vice versa, is included in the invention.

A "purified nucleic acid", as used herein, refers to a nucleic acid sequence or fragment that has been purified from the sequences that flank it in a naturally occurring state, e.g., a DNA fragment that has been removed from the sequences that are adjacent to the fragment, e.g., from the sequences adjacent to the fragment in its normal site in the genome. The term also applies to nucleic acids that have been substantially purified from other components, such as proteins, that naturally accompany it in the cell.

"Homologous", as used herein, refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, if 6 of 10 of the positions in two sequences are matched or homologous then the two sequences are 60% homologous. By way of example, the DNA sequences 3'ATTGCC'5 and 3'TATGGC'5 share 50% homology.

DESCRIPTION OF THE PREFERRED EMBODIMENTS

The drawings will first briefly by described.

DRAWINGS

FIG. 1 is a representation of the amino acid sequence of the canine parietal cell gastrin receptor (SEQ ID NO: 5). The putative transmembrane domains of the gastrin receptor are underlined and indicated by Roman numerals. Consensus N-linked glycosylation sites are indicated by #. Potential protein kinase C or casein kinase II sites, as predicted by patterns found in the Prosite database (Bairock, A., 1991, *Nucleic Acids Res* 19:2241) are indicated by ^.

FIGS. 2A–2B are a representation of the primary structure of the canine parietal cell gastrin receptor and alignment with known G-protein coupled receptors. Shaded amino acids are identical in 2 of the 3 receptors. Bars over the sequences represent transmembrane segments predicted by the KKD algorithm. Abbreviations: FC5, neuropeptide Y-Y1 receptor; hB2AR, human β2 adrenergic receptor.

FIG. 3 is a graph of the effect of competitor concentration on $^{125}$I-CCK-8 binding. Each point represents the mean of three experiments. Maximum binding in the absence of competitor (100%) was 5.2±2.0 pM. Untransfected cells showed no saturable binding.

FIG. 4 is an autoradiograph showing affinity labeling of the canine parietal cell gastrin receptor on transfected COS-7 cells using bifunctional chemical crosslinking. Results are typical of 4 similar experiments.

FIG. 5 is an autoradiograph showing Northern blot analysis of gastrin receptor transcripts in mRNA isolated from canine tissues. Poly(A)$^+$ RNA was loaded as follows: liver, 1.1 μg; parietal cels, 0.3 μg; pancreas, 0.5 μg; and cerebral cortex, 1.0 μg. The transcript corresponding to GR-1 is indicated by an arrow.

FIGS. 6A–6B are a graph showing second messenger signaling in transfected COS-7 cells after stimulation by gastrin (1 μM). A. The arrow indicates the addition of gastrin I. Data shown are representative of 3 experiments. B. Ins-1,4,5-P$_3$ measurements (mean±sem of n=3) in wild type and GR-1 transfected COS-7 cells.

FIG. 7 is a representation of the nucleic acid sequence of the gastrin receptor cDNA GR-1 (SEQ ID NO: 1).

FIGS. 8A–8B are a representation of: A. 66 nucleotides of the CCK-B cDNA (SEQ ID NO: 2); B. The 22 amino acids predicted from the nucleotide sequence of FIG. 8A, compared with the corresponding amino acid sequence of the GR-1 cDNA (amino acids 281–302 of FIG. 1, SEQ ID NO: 3, SEQ ID NO: 5).

FIG. 9 is a representation of the nucleic acid sequence of the human CCK-B receptor cDNA hCCKB (SEQ ID NO: 4).

FIG. 10 is a representation of the amino acid sequence of the human CCK-B receptor (SEQ ID NO: 6).

Figure 11A:
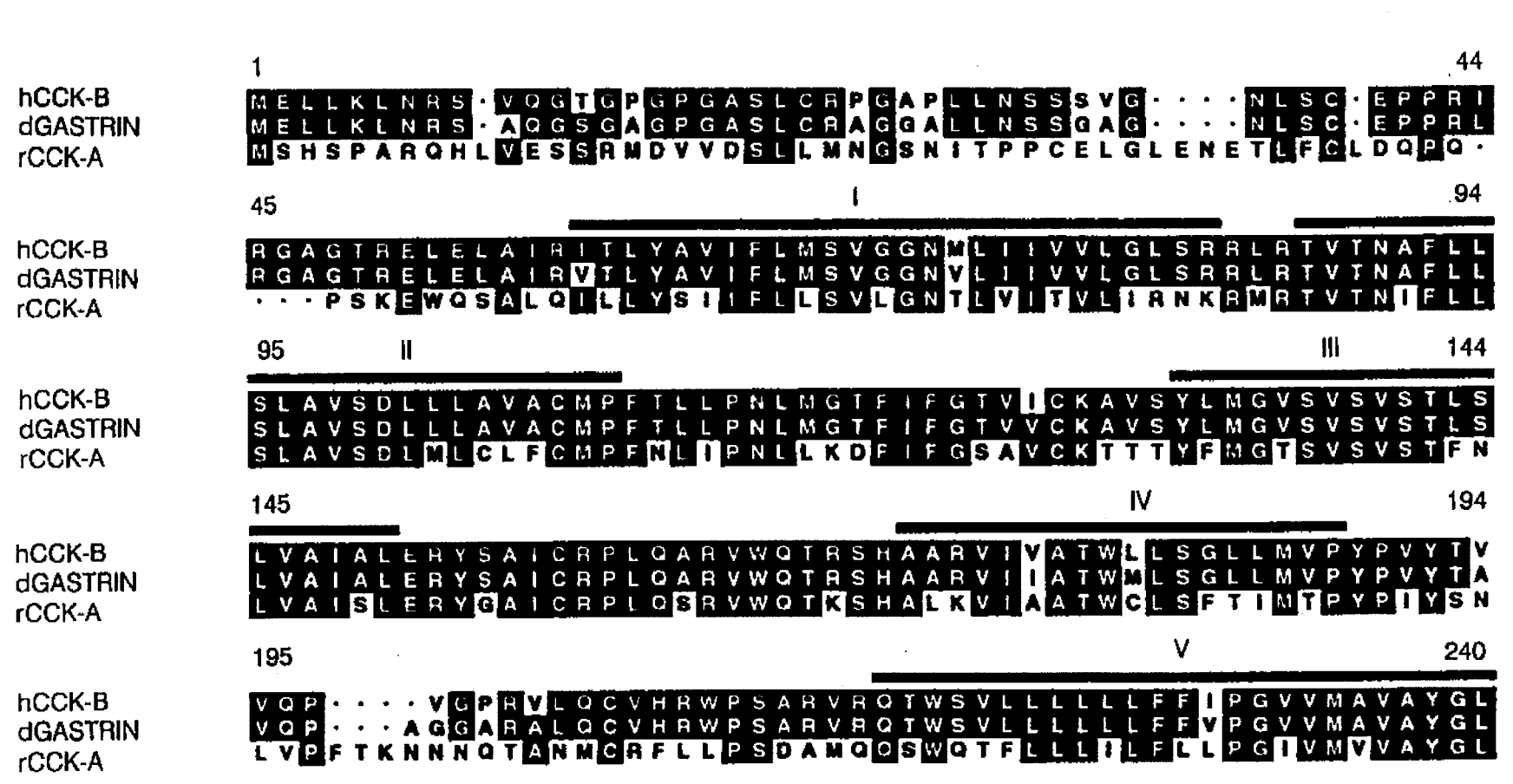

FIGS. 11A–11B are a representation of the amino acid sequence of the human brain CCK-B receptor and alignment with the canine gastrin and the rat CCK-A receptors. Shaded amino acids are identical in at least 2 of the 3 receptors. Bars over the sequences represent transmembrane segments predicted by the KKD algorithm (Klein et al. 1985. *Biochem. Biophys Acta* 815:468–76). Numbering corresponds to amino acids in the CCK-B receptor. Abbreviations: hCCK-B, human CCK-B receptor; dGASTRIN, dog gastrin receptor, rCCK-A, rat CCK-A receptor.

Figure 12:
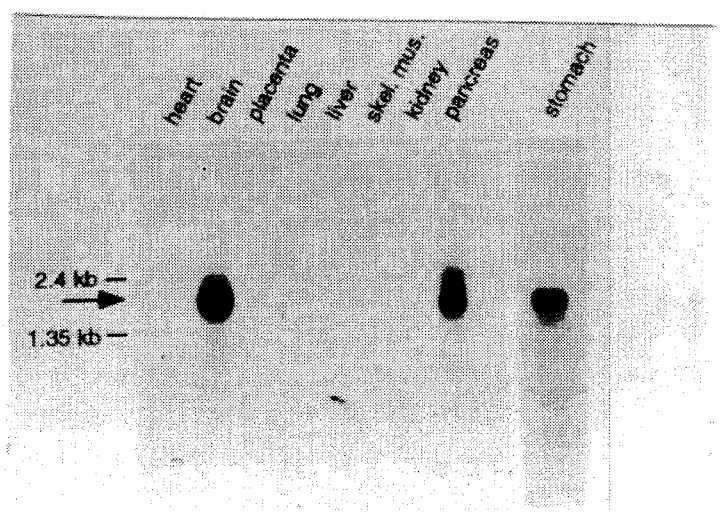

FIG. 12 is an autoradiograph showing Northern blot analysis of CCK-B transcripts in mRNA isolated from human tissues. Poly(A)$^+$ RNA was loaded in each lane as indicated. The transcript corresponding to the CCK-B receptor is indicated by an arrow.

Figure 13A:
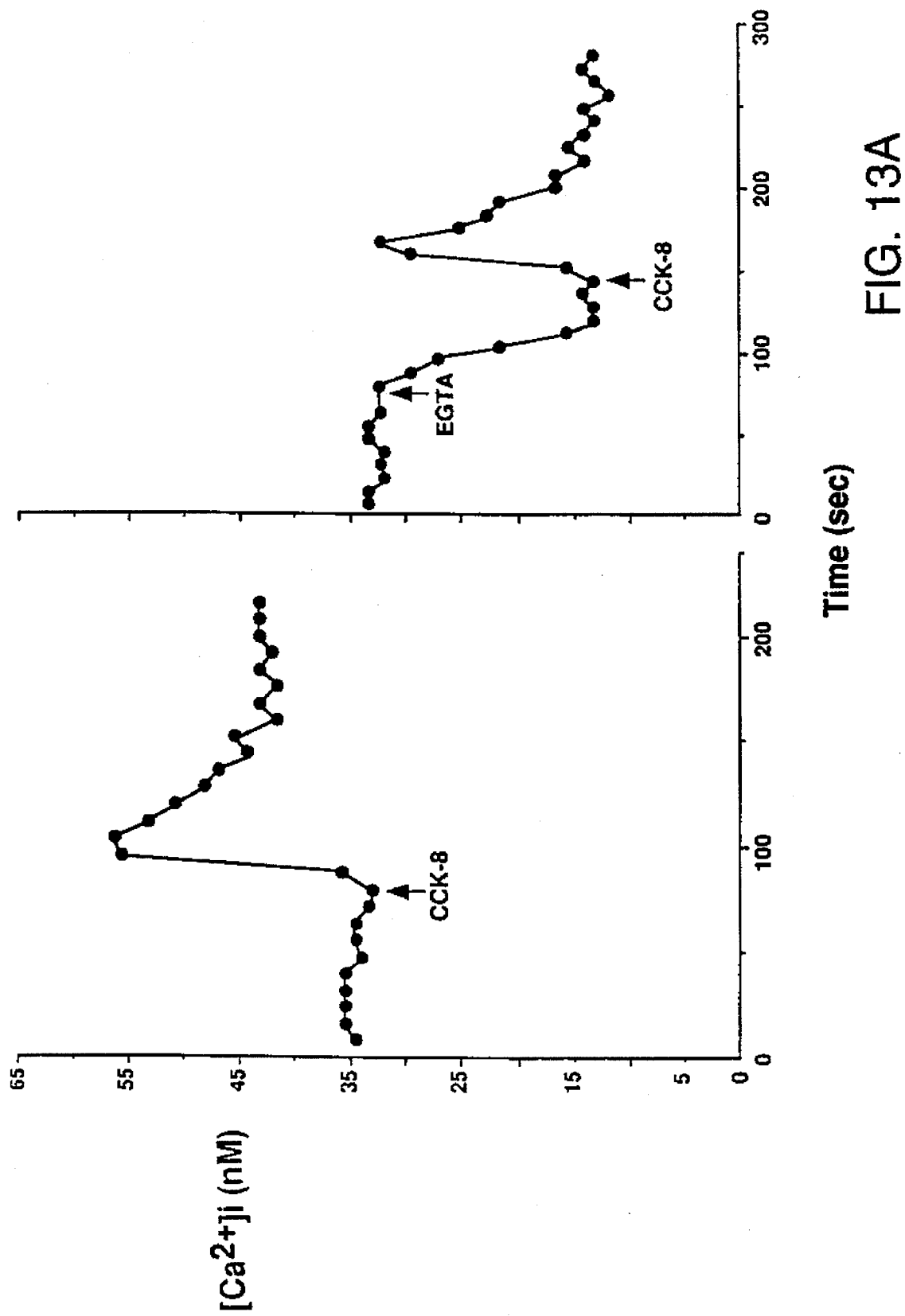
Figure 13B:
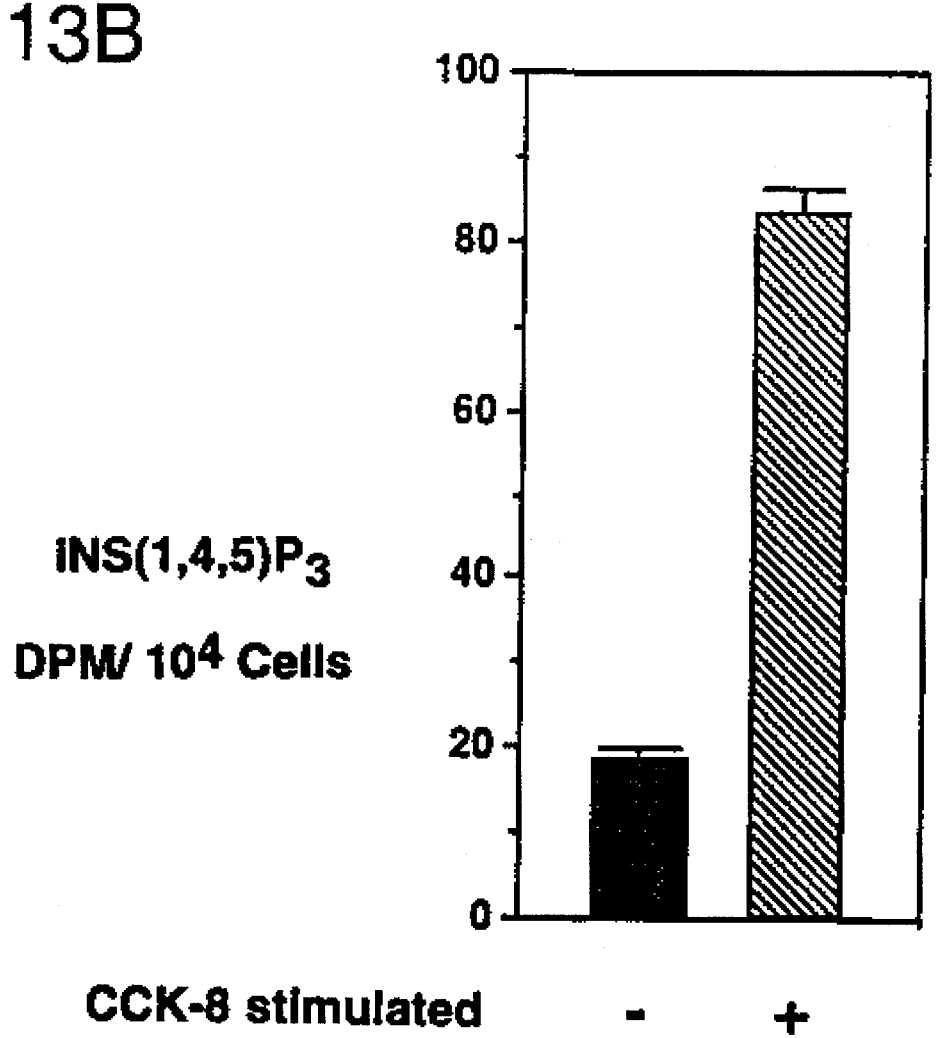

FIGS. 13A–13B are a graph showing second messenger signaling in COS-7 cells expressing the recombinant human brain CCK-B receptor. A. In Fura-2 loaded COS-7 cells, free cytosolic calcium concentration was determined from fluorescence emission ratios at 340/380 nm. The arrows indicate the addition of CCK-8 (0.1 μM) or EGTA (2.5 mM). Data shown are representative of 3 experiments. B. CCK-8 (0.1 μM) increased Ins-1,4,5-P$_3$ levels (mean±SEM of n=3) in COS-7 cells transfected with the CCK-B receptor cDNA from 1,834±119 to 8,303±275 DPM/$10^6$ cells (p<0.001).

Figure 14A:
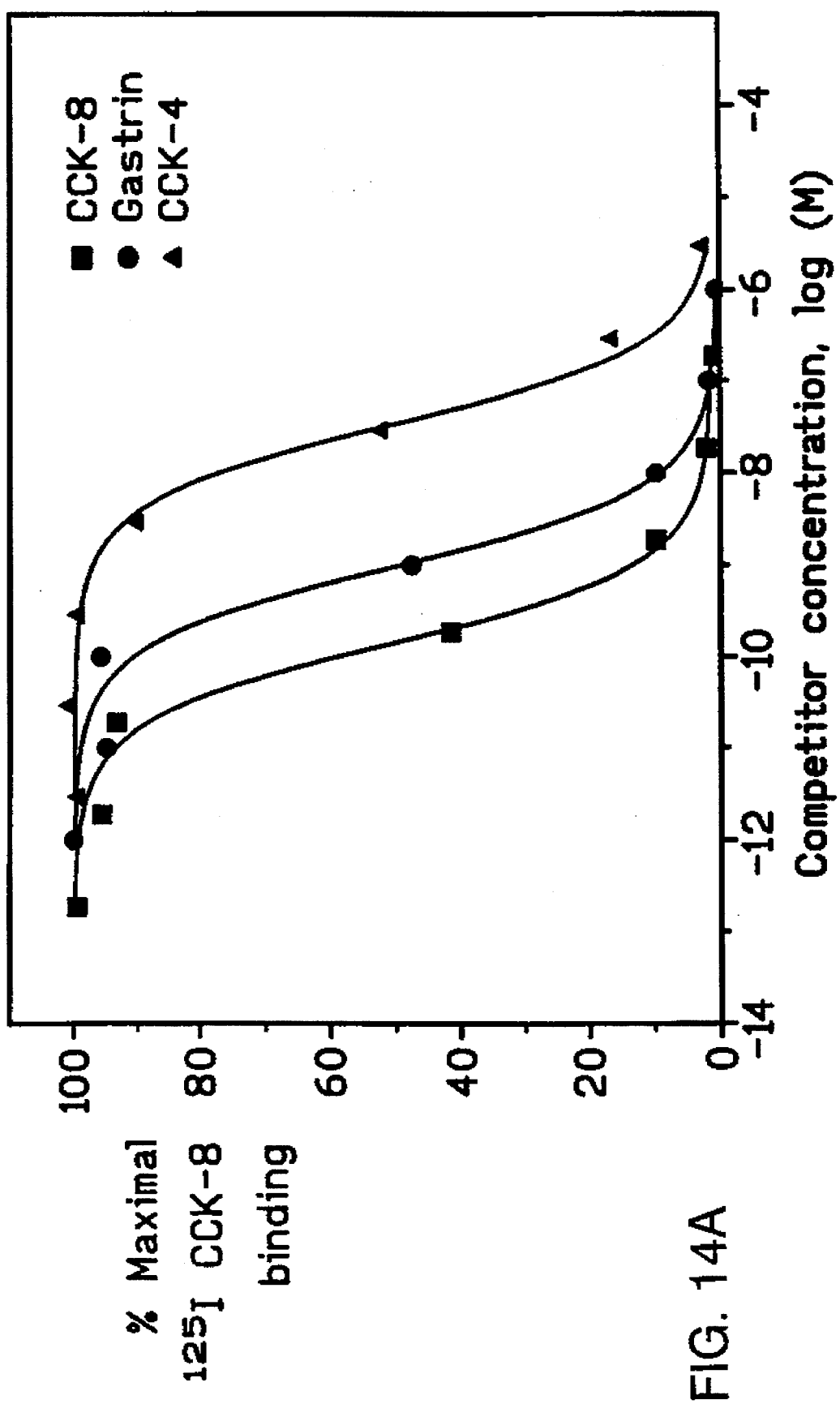
Figure 14B:
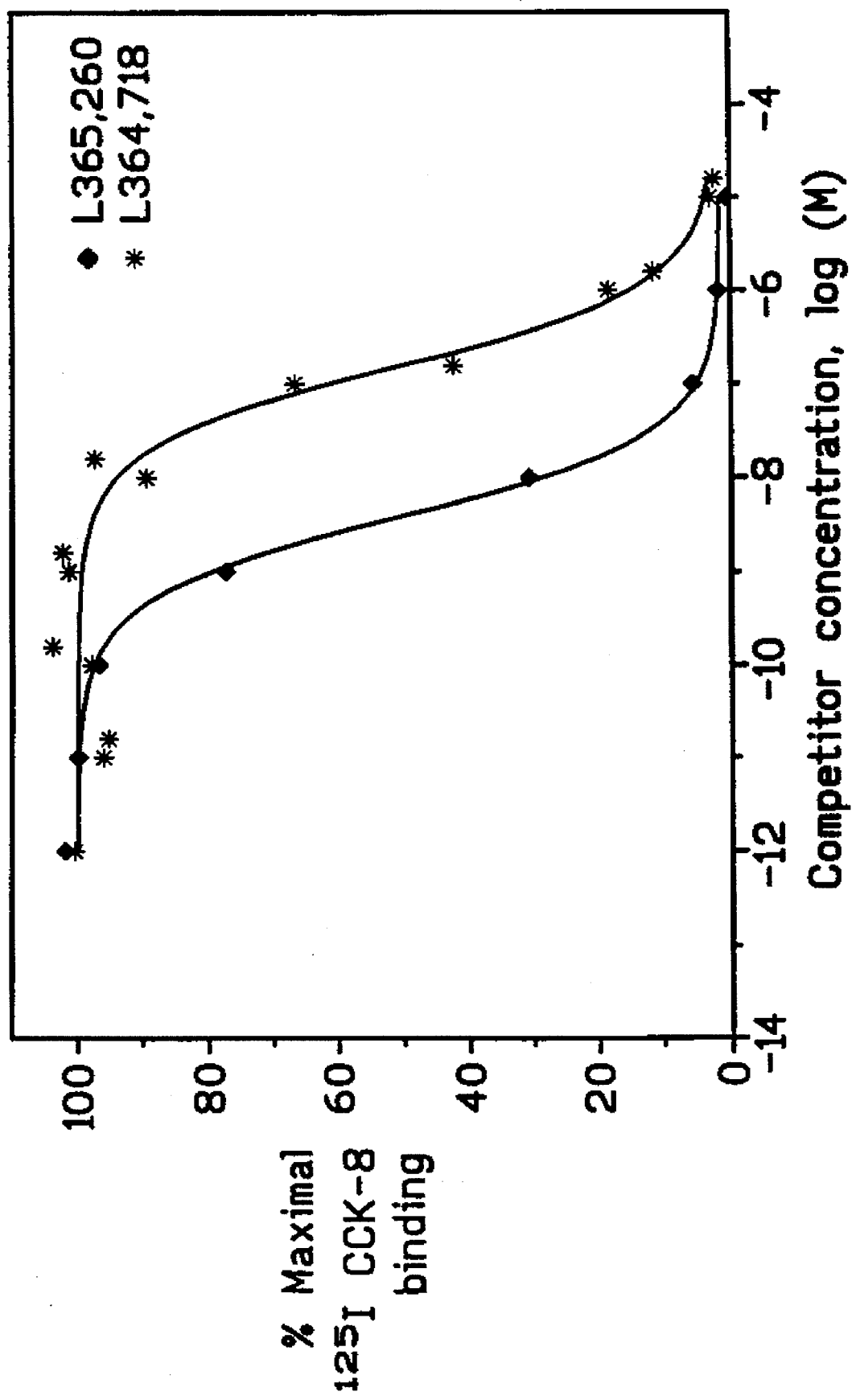

FIGS. 14A–14B are a graph showing the effect of competitor concentration on $^{125}$I-CCK-8 binding to the CCK-B receptor. Binding of $^{125}$I CCK-8 to COS-7 cells, transiently transfected with hCCK-B-pcDNAI, is shown in the presence of increasing concentrations of: (A) CCK-8, Gastrin, CCK-4; and (B) L364,718, and L365,260. Each curve represents the mean of 3–5 experiments. Untransfected cells showed no displaceable binding.

DERIVATION OF DEPOSITED MATERIALS

Plasmid clones GR-1, HBR-1, and hCCK-B have been deposited with the American Type Culture Collection (A.T.C.C.) in Rockville, Md., and they, respectively, bear the accession numbers: ATCC No. 75195, No. 75196, and No. 75303. These deposits allow others skilled in the art to readily obtain the materials of this invention. The derivation of these deposited materials is described below. The gastrin receptor and CCK-B receptor produced by these deposited materials is exemplary of, not limiting to, this invention; those of ordinary skill in the art can readily isolate equivalent recentors, and nucleic acid encoding such receptors, using the methods described below. Applicant's assignee, the President and Fellows of New England Medical Center Hospital, acknowledge their responsibility to replace these cultures should they die before the end of the term of a patent issued hereon, and their responsibility to notify the ATCC of the issuance of such a patent, at which time the deposits will be made available to the public. Until that time the deposits will be made available to the Commissioner of Patents under the terms of 37 CFR §1.14 and 35 USC §112.

DETAILED DESCRIPTION

The following procedure was undertaken to construct a canine parietal cell cDNA expression library, isolate the gene for the gastrin receptor from canine parietal cells, and confirm the identity and biological activity of the resulting recombinant clone. The recombinant receptor was isolated from a library produced from a highly enriched preparation of parietal cells. Northern blot analysis of mRNA from isolated parietal cells shows that the gastrin receptor transcript (GR-1) is highly expressed in these cells. To determine whether the biological activity of the recombinant receptor was consistent with that of native canine parietal cells, binding assays of agonists and antagonists, affinity labeling and signal transduction assays were used.

The cloned gastrin receptor cDNA was used in turn to isolate the human CCK-B cDNA and gene.

Construction of a Canine Parietal Cell cDNA Expression Library

To isolate canine parietal cells, cells were enzymatically dispersed as described (Soll, A. H. et al., 1984, *J Clin Invest* 73:1434–47). Isolated cells were enriched in a Beckman XJ-10 elutriation system and collected at 900 rpm between flow rates of 50 and 80 ml/min. Further enrichment to 95% purity, as estimated by Papanicolaou staining, was achieved by isopycnic density centrifugation over a discontinuous Percoll® gradient.

RNA was prepared from approximately $1.5 \times 10^8$ parietal cells by acid phenol extraction (Chomczynski, P. et al., 1987, *Anal Biochem* 162:156–9) followed by oligo(dT)-cellulose chromatography. Six μg of poly($A^+$) RNA were converted to double stranded cDNA (Aruffo, A., et al., 1987, *PNAS* 84:8573–7). Following addition of BstX1 adaptors (InVitrogen, San Diego), the cDNA was size selected over a 5–20% potassium acetate gradient and fractions greater than 1.5 kb were ligated into the expression vector, pCDNA-1 (InVitrogen, San Diego).

Isolation of a Canine Gastrin Receptor cDNA

To isolate a gastrin receptor clone from a canine parietal cell cDNA expression library, $2 \times 10^6$ primary recombinants in pools of 3,000–10,000 were produced by transforming *Escherichia coli* MC1061/p3 by electroporation (Lin, H. Y., et al., 1991, *PNAS* 88:3185–9). Miniprep DNA representing each pool was prepared by the alkaline lysis procedure, and then transfected into COS-7 cells adherent to glass flaskettes (Nunc) using DEAE-dextran (Pacholczyk, T., et al., 1991 *Nature* 350:350–354). Bacterial stocks representing each pool were stored in glycerol. Forty-eight hours following transfection, cells were incubated for 60 min at 37° C. in Hank's buffer supplemented with 25 mM HEPES (pH 7.4), 0.1% BSA (solution A), 50 pM $^{125}$I-CCK-8 (New England Nuclear, 2,200 Ci/mmole) and 50 pM $^{125}$I-D-Tyr-Gly [(Nle$^{28,31}$)-CCK-26-33], a CCK analog that includes a free amino group available for fixation (Pearson, R. K., et al., 1987, *Biochem Biophys Res Commun* 147:346–53). After four washes in ice-cold solution A, cells were fixed in phosphate-buffered saline (pH 7.4)/2.5% glutaraldehyde, dipped in 0.5% gelatin and dried at 37° C. Slides were exposed to Kodak NTB2 photoemulsion for 3 days (Gearing, D. P., et al., 1989, *Embo J* 8:3667–76) and examined by darkfield microscopy. The positive pool was sequentially divided until a single positive clone (GR-1) was obtained.

Nucleotide Sequence of the Canine Gastrin Receptor Clone, GR-1

The gastrin receptor cDNA was subcloned into M13mp18/19 and single stranded templates from both strands were sequenced by the chain termination method (Tabor, S. & Richardson, C. C., 1987, *PNAS* 84:4767–71) using modified T7 DNA polymerase (United States Biochemical Corp.) (FIG. 7 and SEQ ID NO: 1). The sequence was analyzed by the UWGCG program GAP (Devereux, J., et al., 1984, *Nucleic Acids Res.* 12:387–395), and the KKD analysis of hydropathy (Klein, P., et al., 1985, *Biochem Biophys Acta* 815:468–76). The cDNA has an open reading frame encoding a 453 amino acid protein, with a predicted molecular weight of 48,518 (FIG. 1, SEQ ID NO: 5). Hydropathy analysis reveals seven hydrophobic segments, corresponding to the transmembrane domains characteristic of the G-Protein coupled receptor family. Examination of other regions of the deduced amino acid sequence reveals a large number of the amino acid "signatures" present in the vast majority of G-protein coupled receptors. The amino terminus of the cloned receptor lacks a signal sequence, although it includes three potential asparagine-linked glycosylation sites (N-X-S/T) at amino acid positions 7, 30, and 36.

The gastrin receptor shares significant amino acid identity with the β-adrenergic G-protein coupled receptor family (FIGS. 2A–2B). For example, the third cytoplasmic loop and the carboxyl-terminus are rich in threonine and serine residues as potential sites of regulation analogous to those found in rhodopsin and in the β2-adrenergic receptor (Dohlman, H. G., et al., 1991, *Ann Rev Biochem* 60:653–88). There are two cysteine residues (C127 and C206) that may be involved in an intrachain disulfide bond similar to that found in rhodopsin (Karnik, S. S., et al., 1989, *PNAS* 85:8459–63). Translated GR-1 has a high degree of amino acid identity (35%) with the neuropeptide Y-Y1 receptor, FC-5. Additional receptors that have high amino acid identity with the gastrin receptor include the human dopamine D4 receptor (28%), *Drosophila melanogaster* 5HT receptor (27%), and the human β2 adrenergic receptor (26%). Phylogenetic analysis reveals that GR-1 defines a new branch of the neuropeptide ligand class of G-protein coupled receptors.

GR-1 Northern Blot Hybridization Assays

The tissue distribution of GR-1 (FIG. 5) was assessed by high stringency Northern blot analysis. Poly($A^+$) RNA from adult canine tissues was separated on a 1.2% agarose/0.66M formaldehyde gel. The RNA was transferred to Nytran™ membranes by capillary blotting. Filters were hybridized at a high stringency, in a buffer containing 50% formamide (v/v), with a 1,400-base Pst1-Xba1 fragment of the gastrin receptor cDNA, labeled by priming with random hexamers (Feinberg, A. P. & Vogelstein, B., 1983, *Anal Biochem* 132:6–13). The autoradiogram was exposed for 45 hours with 2 intensifying screens at −80° C.

Figure 5:
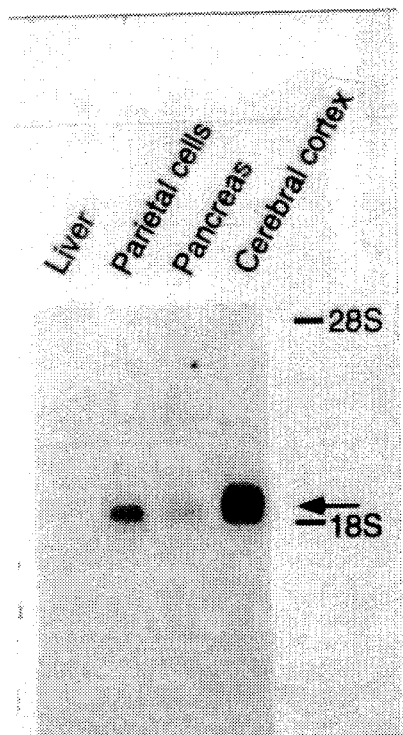

Receptor mRNA was detected in gastric parietal, pancreas and cerebral cortex cells (FIG. 5). The high stringency at which the Northern blots were hybridized provides a good indication that the gastrin and CCK-B receptors are highly homologous. All of these tissues are reported to have gastrin/CCK-B type receptors (Jensen, R. T., et al., 1990, in *Gastrointestinal Endocrinology: Receptors and Post-Receptor Mechanisms*, Harcourt Brace Jovanovich, San Diego p. 95–113; Fourmy, D., et al., 1987, *Eur J Biochem* 165:683–92). The canine pancreas is notable for substantial amounts of CCK-B/gastrin receptors relative to other species.

GR-1 Affinity Crosslinking

The recombinant receptor in GR-1 transfected COS-7 cell membranes was affinity labeled to determine if it is identical in size to the receptor previously described on native canine parietal cells.

For affinity labeling the recombinant receptors, on COS-7 cell membranes from GR-1 transfected cells, were allowed to bind $^{125}$I-D-Tyr-Gly-[(Nle)-CCK-26-33] for 60 min at 22° C., followed by separation of bound from free radioligand by centrifugation (Pearson, R. K., et al., 1987, *Biochem Biophys Res Commun* 147:346–53).

Figure 4:
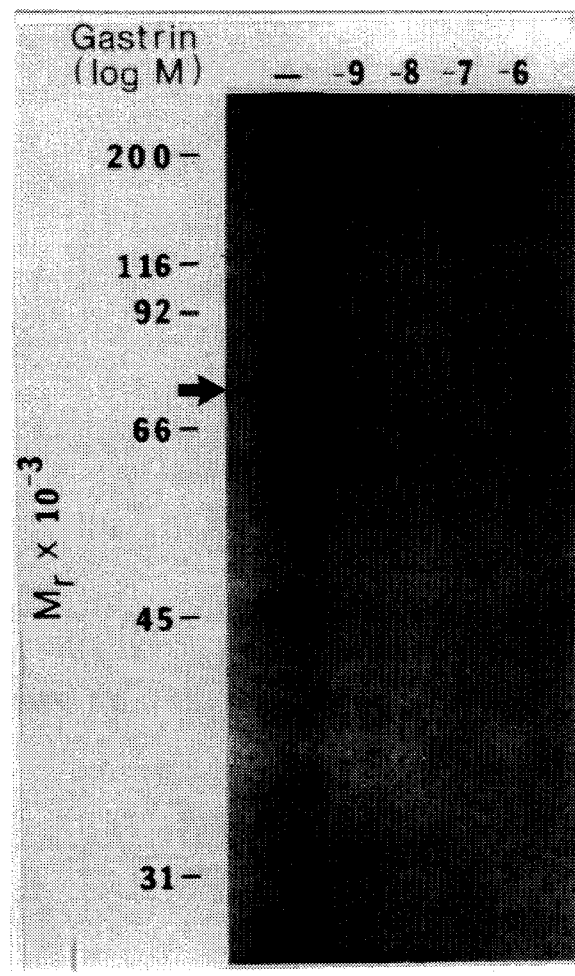

The membrane pellet was cross-linked using 100 μM disuccinimidyl suberate at 4° C. for 5 min, with excess cross-linker quenched with Tris buffer. Labeled membranes were separated on a 10% SDS-PAGE gel, and visualized by autoradiography. These results demonstrate a protein centered at approximately Mr=76,000 (FIG. 4). The broad nature of this band is consistent with its representing a glycoprotein. Indeed, carbohydrate probably accounts for the large difference in molecular weight between the putative core protein and the apparent size of the affinity-labeled band. The size is in agreement with previous affinity labeling data from native canine parietal cells (Matsumoto, M., et al., 1987, *Am J Physiol* 252:G143–G147).

Binding to the GR-1 Receptor

The binding properties of the recombinant GR-1 receptor were characterized to determine whether they were typical of CCK-B/gastrin receptors. COS-7 cells ($1.5 \times 10^6$) were plated in 10 cm culture dishes (Nunc) and grown in DMEM/10% fetal calf serum, 5% $CO_2$ at 37° C. After an overnight incubation, cells were transfected with 5 μg of GR-1 (Pacholczyk, T., et al., 1991, *Nature* 350:350–354). Twenty-four hours following transfection, cells were split into 24-well dishes (Nunc), 5000 cells/well. After an additional 24 hours, competition binding experiments were performed in solution A supplemented with 0.15 mM PMSF and 40 pM $^{125}$I-CCK-8 as radioligand. Equilibrium binding occurred after incubation for 80 min at 37° C. Cell monolayers were subsequently washed three times and bound radioactivity was quantified after cell hydrolysis in 1N NaOH. Radioligand saturation experiments were performed in an analogous manner over a range from 2.5 to 1,000 pM $^{125}$I-CCK-8 (NEN) with non-displaceable binding in the presence of excess unlabeled competitor assessed in parallel wells.

Binding parameters were also measured in isolated plasma membranes from COS-7 cells transfected with GR-1. Binding was performed for 60 min at 22° C. Separation of bound and free radioligand was achieved by receptor-binding filtermat filtration, as previously described (Klueppelberg, U. G., et al., 1989, *Biochemistry* 28:3463–8).

Analyses of competition and saturation binding data were performed using computerized non-linear curve fitting (McPherson, G. A., 1985, *J Pharmacol Methods* 14:213–28).

Pharmacologic characterization of receptors expressed on GR-1 transfected COS-7 cells demonstrated binding specificity typical of CCK-B/gastrin receptors (Matsumoto, M. et al., 1987, *Am J Physiol* 252:G143–G147). $^{125}$I-CCK binding revealed a single homogeneous class of receptors, as confirmed by a Hill slope near unity (0.93±0.07) for homologous competition using unlabeled CCK. Other structurally-related members of this hormone family competed for binding of $^{125}$I-CCK in a concentration-dependent manner. The calculated $IC_{50}$'s for CCK-8, gastrin, and CCK-8-desulfate were 0.09 nM, 0.26 nM, and 1.4 nM, respectively. This is consistent with the radioligand affinity, as derived from saturation binding experiments in GR-1 transfected COS-7 cells ($K_d$=0.08 nM) and in native parietal cells ($K_d$=0.27 nM). Comparable results were obtained using isolated membranes prepared from transiently transfected COS-7 cells ($IC_{50}$'s for CCK-8, gastrin, and CCK-8-desulfate were 0.08 nM, 0.4 nM, and 1.5 nM, respectively.) The same affinity rank order for all tested agonists was confirmed using $^{125}$I-gastrin (Amersham) as the radioligand.

The non-peptide gastrin/CCK receptor antagonists, L364,718 ($IC_{50}$=19 nM) and L365,260 ($IC_{50}$=130 nM) bound to the recombinant receptor (FIG. 3) with affinities similar to those reported for native canine parietal cells. Again, comparable results are obtained using $^{125}$I-CCK or $^{125}$I-gastrin as radioligands in intact GR-1 transfected COS-7 cells or on isolated membranes from these cells. In guinea pig brain, gastric gland membranes, and rabbit parietal cells, all tissues with abundant CCK-B/gastrin receptors, the potency rank order of these antagonists is reversed (Chang, R. S. & Lotti, V. J., 1986, *PNAS* 83:4923–6; Roche, S. et al., 1991, *Am J Physiol* 260:G182–8).

Activation of the GR-1 Recombinant Receptor

Gastrin binding to the recombinant receptor elicits a typical increase in the intracellular calcium concentration and in phosphatidylinositol hydrolysis. This biological response in GR-1 transfected COS-7 cells was used to provide further confirmation that GR-1 encodes a functional receptor protein.

Measurement of [Ca$^{2+}$] Triggered by the GR-1 Receptor

Forty-eight hours after transfection, COS-7 cells were loaded with the Ca$^{2+}$ fluorophore, fura-2, in modified KRB buffer. Fluorescence changes after stimulation of cells with $10^{-6}$M gastrin were measured at A$_{340}$/A$_{380}$ nm, as previously described (Rajah, A. S., et al., 1989, *Diabetes* 38:874–80).

Figure 6A:
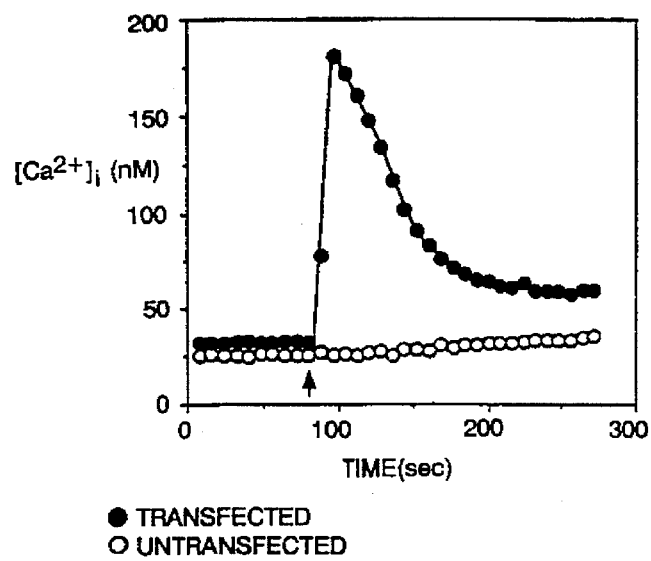

Gastrin ($10^{-6}$M) triggered a marked increase in free cytosolic calcium, [Ca$^{2+}$], from 46.5±6.9 nM to 142.4±16.2 nM (n=3, P<0.05) whereas untransfected cells did not show a response (FIG. 6A). After chelation of extracellular calcium by EGTA (2.5 mM), gastrin transiently increased [Ca$^{2+}$] from 17.6±1.0 to 88.5±11.6 nM (n=3, P<0.05), suggesting that the gastrin-induced increase in [Ca$^{2+}$] originated primarily from intracellular [Ca$^{2+}$] pools.

Measurement of Phosphoinositides Triggered by the GR-1 Receptor

The pattern of [Ca$^{2+}$] response suggests that the recombinant receptor triggers intracellular signalling through activation of phospholipase C; this was confirmed by measurement of phosphoinositide metabolites.

GR-1 transfected COS-7 cells were cultured for 24 hr in inositol-free DMEM (GIBCO), supplemented with 10 µCi/ml [$^3$H](myo)-inositol (ARC) prior to analysis. After 1 hour equilibration in modified KRB (see above), the cells were stimulated with $10^{-6}$M gastrin for 10 sec and harvested in methanol:HCl. The aqueous phase was extracted with chloroform, lyophilized dry, and analyzed by strong anion exchange HPLC (Auger, K. R., et al., 1989, *Cell* 57:167–75).

Figure 6B:
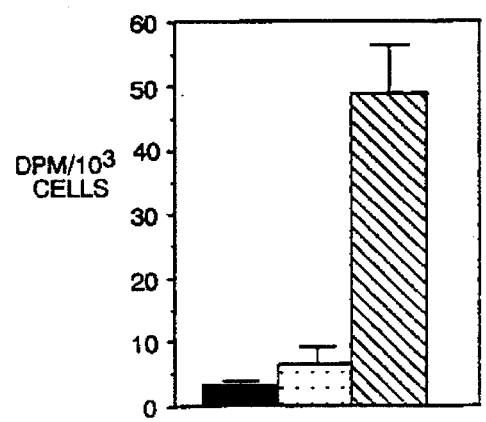

A measurement of phosphoinositide metabolites in GR-1 transfected COS-7 cells was taken 10 sec after gastrin stimulation (FIG. 6B). The time point was chosen to precede the gastrin-induced [CA$^{2+}$] Gastrin ($10^{-6}$M) increased the level of Ins-1,4,5-P$_3$ by 741±115% over control (GR-1 transfected COS cells without stimulation). Ins-1,3,4,5-P$_4$ which may, together with Ins-1,4,5-P$_3$, modulate intracellular calcium levels, also increased by 272±15%, (n=3, P<0.01). These results are in agreement with previous reports of the second messenger pathways linked to the native parietal cell gastrin receptor (Muallem, S. et al., 1984, *Biochim Biophys Acta* 805:181–5; Chew, C. S. et al., 1986, *Biochim Biophys Acta* 888:116–25; Roche, S. et al., 1991, *Febs Letts* 282:147–51). Preliminary evidence suggests that the gastrin receptor, expressed in COS-7 cells, is additionally linked to stimulation of adenylate cyclase.

The binding of agonists and antagonists, the affinity labeling, and the signal transduction data are all indistinguishable from previous observations using native canine parietal cells, that have been shown to have a single homogenous class of receptors. The abundance of the GR-1 transcript both in canine cortex and parietal cells (FIG. 5), supports the idea that "CCK-B" and "gastrin" receptors are highly homologous.

Construction of a Human Parietal Cell cDNA Expression Library, and Isolation of the Human Gastrin Receptor cDNA Human parietal cells or chief cells, which are known to be enriched in CCK-B receptors, can be used to construct a human cDNA expression library. The same methods used to prepare the canine parietal cell cDNA expression library are used to prepare a human parietal or chief cell cDNA expression library, with the exception that cDNA segments are ligated into λgt10 or λgt11 vectors, as described (Sambrook, et al. 1989. *Molecular Cloning: A Laboratory Manual*, 2nd ed. Cold Spring Harbor Lab. Press, 2:8.36–38). Purified nucleic acid from the GR-1 clone of this invention is used as a nucleic acid probe to isolate the human gastrin receptor cDNA.

Isolation and Sequence Analysis of a Human CCK-B Receptor cDNA (hCCRB)

A 1,400-bp PstI-XbaI restriction fragment encoding the 3' end of the canine parietal cell gastrin receptor, radiolabeled with [α-$^{32}$P] dCTP by priming with random hexamers (Feinberg, A. P., et al., 1983, *Anal Biochem*, 132:6–13), was used as a hybridization probe to screen a human brain λDR2 cDNA library (Clontech) (Benton, W. D., et al., 1977, *Science*, 196:180–182). Filters were hybridized overnight at 55° C. in 5× SSC (1× SSC is 0.15M naCl/0.015M sodium citrate, pH 7.0) and washed in 2× SSC/0.1% SDS at the same temperature. Of 4×10$^6$ primary recombinants screened, a single positive clone was identified. After plaque purification, the corresponding cDNA insert (~1 kb) was subcloned into the expression vector pcDNA I (Invitrogen, San Diego, Calif.) and sequenced by the chain termination method (Tabor, S., et al., 1987, *PNAS*, 84:4767–4771) using a modified T7 DNA polymerase (United States Biochemical Corp.). Sequence comparison with the canine gastrin receptor cDNA using the UWGCG software programs (Devereux, J., et al., 1984, *Nucleic Acids Res*, 12:387–395) suggested that the initial clone was a fragment corresponding to the 3' end of the putative CCK-B receptor cDNA. DNA from the plaque was purified and sequenced as described for the GR-1 clone. The sequence of 66 base pairs within the open reading frame is shown in FIG. 8A (SEQ ID NO: 2). SEQ ID NO: 2 also shows the corresponding predicted amino acid sequence of the CCK-B cDNA. These 22 amino acids are found to be highly homologous to the corresponding 22 amino acids of the GR-1 predicted amino acid sequence (#281–302 of SEQ ID NO: 5) as shown in FIG. 8B.

The 1 kilobase cDNA insert was then used as a hybridization probe to isolate the corresponding full length human CCK-B receptor cDNA from a fetal (week 23) human brain library in λLAS, a modified lambda vector (Swaroop, A., et al., 1988, *Nucleic Acids Res*, 16:8739). Approximately 8×10$^5$ primary recombinants were screened using the same conditions described above. Seven of the ten positive clones were plaque purified; the longest insert (hCCKB) was subcloned into pcDNA I and sequenced as described above. The nucleotide sequence was analyzed by UWGCG software programs (Devereux, J., et al., 1984, *Nucleic Acids Res*, 12:387–395).

The human brain CCK-B receptor cDNA encodes a protein of 447 amino acids (FIG. 10, SEQ ID NO: 6) with a predicted molecular weight of 48,419 daltons. Hydropathy analysis and comparison with other known receptors suggest the CCK-B receptor is a member of the seven transmembrane domain, G-protein coupled receptor family. The amino terminus of the receptor includes three potential asparagine-linked glycosylation sites (N-X-S/T) at amino acid positions 7, 30, and 36. The deduced amino acid sequence reveals a number of structural features found in the majority of the known G-protein coupled receptors. Cysteine residues, one in the first extracellular loop (C-127) and one in the second extracellular loop (C-205), have the potential to form an intrachain disulfide bond similar to that found in rhodopsin (Karnik, S. S., et al., 1988, *PNAS*, 85:8459–8463). Serine and threonine residues are clustered in both the third cytoplasmic loop and at the carboxyterminus; these may serve as sites of phosphorylation, analogous to those found in the β-adrenergic receptor and rhodopsin (Dohlman, H. G., et al., 1991, *Eur J Biochem*, 60:653–688).

Comparison with other known G-protein coupled receptors reveals that the deduced amino acid sequence of the CCK-B receptor shares the highest degree of amino acid identity with the canine gastrin receptor (91%) followed by the rat $CCK_A$ receptor (49%). Amino acid sequence alignment of the three putative CCK/gastrin receptor subtypes (FIG. 11) demonstrates the high degree of sequence identity among these receptors not only within the transmembrane domains but also within the extracellular and intracellular loops. Additional receptors which have a high degree of amino acid identity with the CCK-B receptor include the peptide hormone receptors: rat neuropeptide Y (30%), human V2 vasopressin (30%), human oxytocin (28%) and the biogenic amine receptors: human β2-adrenergic (26%) and rat serotonin (23%).

CCK-B Northern Blot Hybridization Assay

Two micrograms of poly(A)$^+$ RNA isolated from nine different human tissues were separated on a denaturing formaldehyde agarose gel and transferred to a nylon membrane (Human MTN blot, Clontech). A 1,400-bp PstI-XhoI fragment of hCCKB, radiolabeled with [$\alpha$-$^{32}$P] dCTP by priming with random hexamers (Feingerb, A. A. et al., 1983, *Anal Biochem*, 132:6–13), hybridized to the membrane overnight at 42° C. in 50% formamide (vol/vol)/5× SSC/20 mM sodium phosphate, pH 6.6/1× Denhardt's solution/0.5% SDS/10% dextran sulfate (wt/vol)/and sheared denatured salmon sperm DNA (100 μg/ml). The membrane was washed for 40 min in 0.2× SSC, 0.1% SDS at 69° C. The blot was reprobed with a human β-actin cDNA probe under the same conditions and washed in 0.2× SSC, 0.1% SDS at 55° C. A strong β-actin autoradiographic signal was observed in all lanes after a three hour exposure (data not shown).

The tissue distribution of the hCCKB transcript was assessed by high stringency Northern blot analysis (FIG. 12). A RNA transcript of approximately 2.2 kb was detected in human brain, stomach, and pancreas, all tissues known by functional and/or receptor binding data to possess CCK/gastrin receptor subtypes. The hybridization signal in mRNA isolated from stomach indicates identity or cross-reactivity with the human parietal cell gastrin receptor transcript. However, it is also possible that the probe hybridizes to another related gastric CCK/gastrin receptor subtype. Two pancreatic signals suggest expression of CCK/gastrin receptors in the pancreas as well. Although not yet reported in man, the canine pancreas has been shown by photoaffinity labeling to have substantial amounts of "gastrin" receptors in addition to CCK-A receptors (Fourmy, D. et al., 1987, *Eur J Biochem*, 165:683–692). Thus, the 2.2 kb hybridization signal most likely represents a pancreatic gastrin or CCK-B receptor transcript. The larger, less intense signal may reflect $CCK_A$ receptor mRNA, an alternately processed variant of the 2.2 kb transcript, or mRNA encoding an as yet unknown, related pancreatic CCK/gastrin receptor subtype.

Measurement of [Ca$^{2+}$]i Triggered by the CCK-B Receptor

Forty-eight hours after transfection with hCCKB-pcDNA I, COS-7 cells were loaded with the Ca$^{2+}$ fluorophore fura-2 in modified Krebs-Ringer bicarbonate buffer. Changes in the fluorescence emission ratios (340/380 nm) after stimulation of cells with 10$^{-7}$M CCK-8 were measured as previously described (Rajah, A. A., et al., 1989, *Diabetes*, 38:874–880).

Measurement of Phosphoinositide Metabolites Triggered by the CCK-B Receptor

Cos-7 cells transfected with hCCKB-pcDNA I were cultured in inositol-free DMEM (GIBCO) supplemented with 10 μCi/ml [$^3$H](myo)-inositol (ARC) for 24 hr. prior to analysis. After 1 hour equilibration in modified Krebs-Ringer bicarbonate (see above) the cells were stimulated with 10$^{-7}$M CCK-8 for 10 seconds and harvested in methanol:HCl. The aqueous phase was extracted with chloroform, lyophilized, and analyzed for inositol 1,4,5-triphosphate (Ins-1,4,5-$P_3$) and inositol 1,3,4,5-tetrakisphosphate (Ins-1, 3,4,5-$P_4$ by strong anion exchange HPLC (Auger, K. R., et al., 1989, *Cell*, 57:167–175).

To confirm that hCCKB encodes a functional receptor, second messenger signaling was measured in response to CCK-8 stimulation of COS-7 cells expressing the recombinant receptor. CCK-8 (10$^{-7}$M) triggered a marked increase in free cytosolic calcium, [Ca$^{2+}$]i, (FIG. 13A, left panel), whereas untransfected cells did not show a response. After chelation of extracellular calcium by 2.5 mM EGTA (1.5 mM Ca$^{2+}$ in the buffer), addition of CCK-8 (10$^{-7}$M) transiently increased [Ca$^{2+}$]i (FIG. 13A, right panel), suggesting that the initial peak of the CCK-induced increase in [Ca$^{2+}$]i originated primarily from intracellular Ca$^{2+}$ pools. The pattern of [Ca$^{2+}$]i response suggests that the binding of CCK-8 to the recombinant receptor triggers intracellular signaling through activation of phospholipase C. This was confirmed by measurement of phosphoinositide metabolites in hCCKB=PCDNA I transfected COS-7 cells 10 seconds after CCK-8 stimulation (FIG. 13B). This time point was chosen to just precede the CCK-8 induced [Ca$^{2+}$]i peak. CCK-8 (10$^{-7}$M) increased the level of Ins-1,4,5-$P_3$ by 453% over control, unstimulated hCCKB-PCDNA I transfected COS-7 cells (n=3, P<0.001). Ins-1,3,4,5-$P_4$, an immediate metabolite of Ins-1,4,5-$P_3$, also increased by 186% over control (n=3, P<0.01). These results further support that the isolated clone encodes a functional brain receptor.

Binding to the CCK-B Receptor

COS-7 (1.5×10$^6$) cells were plated in 10 cm culture dishes (Nunc) and grown in DMEM/10% fetal calf serum, in a 5% CO$_2$/95% air incubator at 37° C. After an overnight incubation, cells were transfected (Pacholczyk, T., et al., 1991, *Nature*, 25:350–354) with 5–7 μg of the pcDNA I expression vector containing hCCKB (hCCKB-pcDNA I). Twenty-four hours after transfection, cells were split into 24-well dishes (2×10$^4$ cells/well (Costar). After an additional 24 hours, competition binding experiments were performed in Hank's buffer supplemented with 25 mM HEPES (pH 7.4), 0.1% bovine serum albumin, and 0.15 mM PMSF. Twenty pM $^{125}$I CCK-8 (New England Nuclear) was used as a radioligand. Equilibrium binding occurred after incubation for 80 min at 37° C. Cell monolayers were then washed three times, hydrolyzed in 1 NaOH, and bound radioactivity was quantified. Unlabeled agonists, CCK-8, gastrin I, CCK-4 (Peninsula) and antagonists, L364,718, and L365,260 (Glaxo), were tested over the concentration range of 0.1 pM- 10 μM. All binding experiments were repeated 3–5 times. The competition data were analyzed using computerized non-linear curve fitting (Inplot 4.0, GraphPad, San Diego, Calif.).

Pharmacologic characterization of the human brain CCK-B receptor expressed in COS-7 cells revealed agonist affinities consistent with a CCK-B type receptor as previously defined using isolated brain membranes (Innis, R. B., et al., 1980, *PNAS*, 77:6917–6921; Saito, A., et al., 1980, *Science*, 208:1155–1156; Lotti, V. J., et al., 1989, *Eur J Pharmacol*, 162:273–280; Hays, S., et al., 1980, *Neuropeptides*, 1:53–62). The structurally related agonists CCK-8, gastrin I, and CCK-4, all competed in a concentration-dependent manner for binding of $^{125}I$ CCK-8 to COS-7 cells expressing the recombinant receptor. The calculated $IC_{50}$ values for CCK-8, gastrin I, and CCK-4 are 0.14 nM, 0.94 nM, and 32 nM, respectively (FIG. 14A). As expected for a "prototype" CCK-B receptor, the recombinant receptor has high affinity for both CCK-8 and gastrin I, with a 7-fold higher affinity for CCK-8. This difference in relative affinities (CCK-8 vs. gastrin I) is in reasonable agreement with the 10-fold difference reported in four studies of guinea pig and rat isolated brain membranes (Innis, R. B., et al., supra; Saito, A., et al., supra; Lotti, V. J., supra; Hays, S., et al., supra). Slight variations in the affinity ratios when comparing earlier studies may be attributed to variability in experimental conditions including tissue preparation protocols, sources of peptides, and radioligands used.

The affinity for CCK-4 provides additional evidence that the recombinant human brain receptor is a CCK-B rather than a $CCK_A$ receptor. In studies utilizing isolated brain membranes from guinea pig (Innis, R. B., et al., supra) mouse, (Hughes, J., et al. 1990, *PNAS*, 87:6728–6732), rat (Saito, A., et al., supra), the IC50 ratio of the CCK-B receptor for CCK-4 (vs. CCK-8) ranged from 10 to 110. The present studies of the human recombinant receptor reveal an IC50 ratio (CCK-4 vs. CCK-8) of 230, consistent with the referenced values described above. In contrast, the CCK-A receptor characterized on rat pancreatic membranes binds CCK-4 (vs. CCK-8) with an IC50 ratio of 30,000–44,000 (Jensen, R. T., et al., 1989, *Trends Pharmacol Sci*, 10:418–423; Hughes, J., et al., supra).

The binding of the nonpeptide antagonists L364,718 and L365,260 to the recombinant receptor further confirms its classification as a CCK-B receptor (Hughes, J., et al., supra; Lotti, V. J., et al., supra; Chang, R. S., et al., 1986, *PNAS*, 83:4923–4926). The IC50 values for L364,718 and L365-260 are 145 nM and 3.8 nM respectively (FIG. 14B). L365,260 bound with approximately 40-fold higher affinity than L364,718, well within the 6 to 125 fold range described in the literature (Hughes, J., et al., supra; Lotti, V. J., et al., supra). The IC50 of the recombinant receptor for L365,260 is also in good agreement with the reference value determined using isolated human brain membranes (2.4 nM) (Lotti, V. J., et al., supra).

Purification of The Gastrin Receptor and CCK-B Receptor Polypeptides

The gastrin receptor and CCK-B receptor polypeptides can be purified using conventional methods of protein isolation known to one schooled in the art, e.g., methods including but not limited to precipitation, chromatography, immunoadsorption, or affinity techniques. The polypeptide can be purified from starting material using the GR-1 cDNA in COS-7 cells as described, using the CCK-B cDNA in COS-7 cells, or using a recombinant form of these cDNAs genetically engineered into an overproducing cell line.

Screening Candidate Antagonists

Gastrin-induced or CCK-induced activation of the gastrin receptor provides an assay for screening candidate antagonists for ones that block a cystolic increase in $[Ca^{2+}]$, an increase in phosphatidylinositol hydrolysis, or an increase in adenyl cyclase activity. For example, candidate antagonists are added to cultured cells, e.g. COS-7 cells, that express the GR-1 or CCK-B receptor cDNA. A gastrin receptor or CCK-B receptor agonist is added to the culture. Agonists include, but are not limited to, gastrin, CCK, CCK-8s, CCK-8d, CCK-4, or CCK-5 (Peninsula Co.). Calcium $[Ca^{2+}]$ or phosphoinositides are measured as described above (FIGS. 6A and 6B). A commercial kit is used to measure cAMP levels (Amersham). Candidate antagonists are identified as ones that block receptor activation, as demonstrated in FIGS. 6A and 6B, or in FIGS. 13A and 13B. Candidate antagonists include peptide and nonpeptide antagonists.

Figure 3:
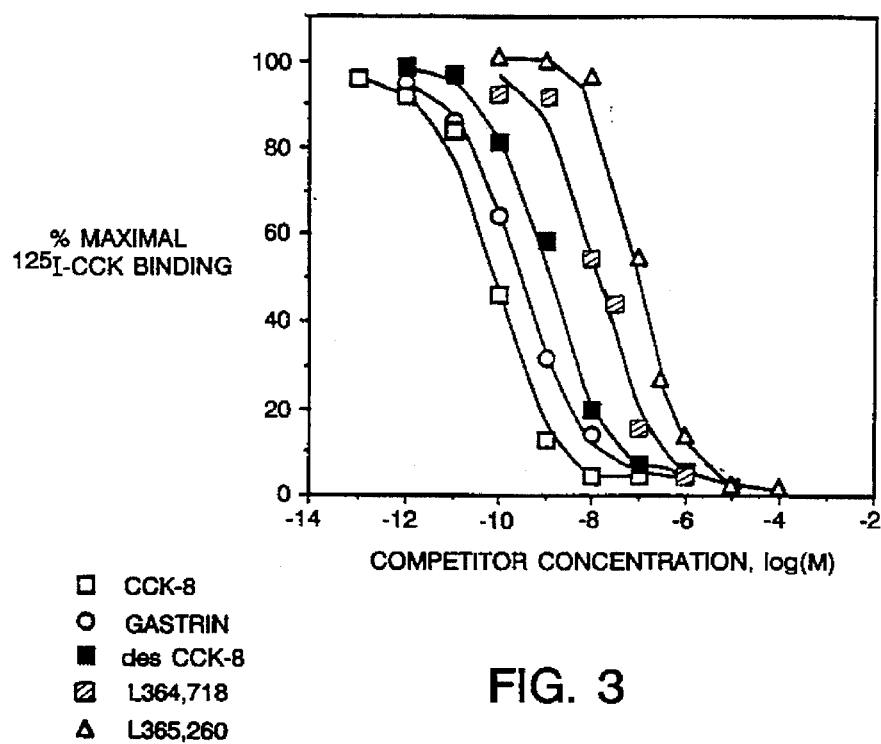

Alternatively, competition binding experiments are performed on COS-7 cells transfected with GR-1 or CCK-B receptor cDNA, as described for FIGS. 3 and 14. Agonist binding to the receptor is measured. These measurements are compared to a control cell sample incubated under identical conditions, but to which no candidate antagonist is added. Useful antagonists are defined as those molecules that inhibit the binding of the agonist to the receptor, as shown in a Hill plot similar to FIG. 3.

Therapy

These antagonists, once identified, can be used therapeutically to inhibit the in vivo activity of the gastrin receptor or the CCK-B receptor. Antagonists of the gastrin receptor can be useful, for example, in the treatment of Zollinger-Ellison syndrome, gastric carcinoma, pernicious anemia, reflux esophagitis, peptic ulcer disease, or carcinoid tumors by decreasing activation of the gastrin receptor and lowering the level of stomach acid. For instance, Omeprazole® (Merck), which is known to lower the level of stomach acid, raises gastrin levels during long-term use, causing carcinoid tumors in rats. A gastrin receptor antagonist could counteract this effect, making it possible to use Omeprazole® for longer periods of treatment. Since gastrin can also be involved in growth and differentiation, gastrin receptor antagonists may be useful for treating certain cancers including, but not limited to, small cell carcinoma of the lung or smooth muscle tumors.

Antagonists to the CCK-B receptor can be used to inhibit the in vivo activity of the CCK-B receptor. Antagonists of the CCK-B receptor may be useful in the treatment of pain, depression and anxiety, memory, satiety or eating disorders, and panic disorders. For example, CCK analogs, e.g., CCK-4, cause panic attacks in humans. If the CCK-B receptor is blocked by, for instance, a CCK-B receptor antagonist, the panic attacks are stopped.

An effective amount of the antagonist, in either case, could be administered intravenously to the patient, incorporated into a slow-release device, or administered orally according to conventional methods.

Other Embodiments

Other embodiments are within the following claims.

For example, other equivalent clones can be isolated by hybridization screening techniques, well known to those of ordinary skill in the art, using cDNAs of the invention to screen canine or human parietal cell cDNA expression libraries; similarly, a purified nucleic acid encoding the prostaglandin $E_2$ receptor may be obtained using these cDNA libraries.

The parietal cell cDNA expression library can be prepared by ligating parietal cell cDNA into other vectors, i.e. vectors other than pCDNA-1, λgt10, or λgt11, able to express biologically active protein products in eukaryotic cells.

The invention includes any protein which is substantially homologous to the canine gastrin receptor (FIG. 1; SEQ ID NO: 5), the human gastrin receptor, and the human CCK-B receptor (FIG. 10; SEQ ID NO: 6) as well as other naturally occurring members of the gastrin/CCK-B receptor family. Also included are: allelic variations; natural mutants; induced mutants; proteins encoded by DNA that hybridizes under high or low (e.g., washing at 2×SSC at 40° C. with a probe length of at least 40 nucleotides) stringency conditions to a nucleic acid naturally occurring The term also includes chimeric polypeptides that include a member of the gastrin/CCK-B receptor family.

The invention also includes any biologically active fragment or analog of a member of the gastrin/CCK-B receptor family. By "biologically active" is meant possessing any in vivo or in vitro activity which is characteristic of the gastrin/CCK-B receptor family. Because the mammalian gastrin/CCK-B receptor family exhibits a range of physiological properties and because such properties may be attributable to different portions of the gastrin/CCK-B receptor molecule, a useful gastrin/CCK-B receptor fragment or analog is one which exhibits biological activity in any gastrin/CCK-B receptor assay, or exhibits any of the following activities: a) the ability of the receptor to bind an agonist, or b) an agonist-induced increase in free cytosolic calcium [Ca+2], or c) an agonist-induced activation of phospholipase C, or d) an agonist-induced activation of adenylate cyclase to increase the level of cAMP. A mammalian gastrin/CCK-B receptor family fragment or analog possessing 10%, preferably 40%, or at least 90% of the activity of a mammalian gastrin/CCK-B receptor polypeptide, (e.g., shown in FIG. 1; SEQ ID NO: 2), in any in vivo or in vitro mammalian gastrin/CCK-B receptor assay, (e.g., those described above), is considered biologically active and useful in the invention.

Putative biologically active fragments of gastrin/CCK-B receptor can be generated by methods known to those skilled in the art. The ability of a candidate fragment to perform the assays listed above can be assessed by methods known to those skilled in the art, e.g., by methods described below.

Preferred analogs include a member of the gastrin/CCK-B receptor family (or biologically active fragments thereof) whose sequences differ from the wild-type sequence only by conservative amino acid substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity. Other useful modifications include those which increase peptide stability; such analogs may contain, for example, one or more non-peptide bonds (which replace the peptide bonds) or D-amino acids in the peptide sequence.

Analogs can differ from naturally occurring gastrin/CCK-B receptors in amino acid sequence, or in modifications that do not affect the sequence, or in both. Analogs of the invention will generally exhibit at least 70%, more preferably 80%, more preferably 90%, and most preferably 95% or even 99%, homology with a segment of 20 amino acid residues, preferably more than 40 amino acid residues, or more preferably the entire sequence of a naturally occurring gastrin or CCK-B receptor sequence.

Alterations in primary sequence include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability can be conferred by cyclizing the peptide molecule. By exposing the polypeptide to phosphorylation-altering enzymes, e.g., kinases or phosphatases modifications include in vivo or in vitro chemical derivatization of polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation affecting enzymes derived from cells that normally provide such processing, e.g., mammalian glycosylation enzymes; phosphorylation can be modified by exposing the polypeptide to phosphorylation-altering enzymes, e.g., kinases or phosphatases.

In addition to substantially full-length polypeptides, the invention also includes biologically active fragments of the polypeptides. As used herein, the term "fragment", as applied to a polypeptide, will ordinarily be at least about residues, more typically at least about 40 residues, preferably at least about 60 residues in length. Fragments of a gastrin or CCK-B receptor can be generated by methods known to those skilled in the art. The ability of a candidate fragment to exhibit a biological activity of a gastrin or CCK-B receptor can be assessed by methods known to those skilled in the art as described herein. Also included are gastrin/CCK-B receptor polypeptides containing amino acids that are normally removed during protein processing, including additional amino acids that are not required for the biological activity of the polypeptide, or including additional amino acids that result from alternative mRNA splicing or alternative protein processing events.

---

I claim:

1. A method for identifying an antagonist to a member of the mammalian gastrin/cholecystokinin-B receptor family, said method comprising:

providing a gastrin/cholecystokinin-B receptor family-specific agonist to cultured eukaryotic cells transfected with a purified nucleic acid that encodes a member of the mammalian gastrin/cholecystokinin-B receptor family of polypeptides in the presence of a candidate antagonist, wherein said candidate antagonist is not prior known to be an antagonist to a member of said gastrin/cholecystokinin-B receptor family; and determining the ability of said candidate antagonist to either, a) interfere with binding of said agonist to said member, or b) block an agonist-induced increase in free cytosolic calcium, or c) block an agonist-induced activation of phospholipase C, or d) block an agonist-induced activation of adenyl cyclase as an indication of antagonist activity.

2. The method of claim 1, wherein said agonist is gastrin.

3. The method of claim 1, wherein said agonist is a cholecystokinin (CCK).

4. The method of claim 3, wherein said agonist is selected from the group consisting of CCK-8s, CCK-8d, CCK-4, and pentagastrin (CCK-5).

5. The method of claim 1, wherein said polypeptide is selected from the group consisting of:

(a) a polypeptide consisting of the amino acid sequence set forth in SEQ ID NO: 5; and (b) a polypeptide consisting of the amino acid sequence set forth in SEQ ID NO: 6.

* * * * *